United States Patent
Park et al.

(10) Patent No.: US 11,272,906 B2
(45) Date of Patent: Mar. 15, 2022

(54) ULTRASONIC IMAGING DEVICE AND METHOD FOR CONTROLLING SAME

(71) Applicant: SAMSUNG ELECTRONICS CO., LTD., Suwon-si (KR)

(72) Inventors: Sung Chan Park, Suwon-si (KR); Jong Keun Song, Yongin-si (KR); Joo Young Kang, Yongin-si (KR); Jung Ho Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 441 days.

(21) Appl. No.: 15/537,717

(22) PCT Filed: Dec. 19, 2014

(86) PCT No.: PCT/KR2014/012581
§ 371 (c)(1),
(2) Date: Jun. 19, 2017

(87) PCT Pub. No.: WO2016/098929
PCT Pub. Date: Jun. 23, 2016

(65) Prior Publication Data
US 2018/0000458 A1  Jan. 4, 2018

(51) Int. Cl.
*G01S 15/89* (2006.01)
*G01S 7/52* (2006.01)
(Continued)

(52) U.S. Cl.
CPC ............ *A61B 8/5276* (2013.01); *A61B 8/145* (2013.01); *A61B 8/4488* (2013.01); *A61B 8/54* (2013.01);
(Continued)

(58) Field of Classification Search
CPC ........ A61B 8/5276; A61B 8/54; A61B 8/4488
See application file for complete search history.

(56) References Cited

U.S. PATENT DOCUMENTS

| | | | | |
|---|---|---|---|---|
| 5,899,861 A | * | 5/1999 | Friemel | .................. G06T 7/246 128/916 |
| 2002/0045824 A1 | * | 4/2002 | Cooley | .................... A61B 8/06 600/443 |

(Continued)

FOREIGN PATENT DOCUMENTS

| JP | 2007513726 A | 5/2007 |
|---|---|---|
| JP | 2007-330764 A | 12/2007 |

(Continued)

OTHER PUBLICATIONS

International Search Report (PCT/ISA/210) dated Sep. 10, 2015 issued by the International Searching Authority in counterpart International Application No. PCT/KR2014/012581.
(Continued)

*Primary Examiner* — Keith M Raymond
*Assistant Examiner* — Milton Truong
(74) *Attorney, Agent, or Firm* — Sughrue Mion, PLLC

(57) ABSTRACT

In accordance with one aspect of the present disclosure, an ultrasound imaging apparatus comprising: an ultrasonic probe for transmitting ultrasonic waves to a target object and receiving ultrasonic waves reflected from the object; a beamforming unit for beamforming the received ultrasonic wave and outputting a beamforming signal; a sampling unit for adjusting the number of sampling times of the beamforming signal according to the amount of motion of the object; and an image processing unit for matching and synthesizing the sampled signals.

15 Claims, 23 Drawing Sheets

(51) Int. Cl.
*A61B 8/14* (2006.01)
*A61B 8/00* (2006.01)
*A61B 8/08* (2006.01)
*G10K 11/34* (2006.01)

(52) U.S. Cl.
CPC ...... *G01S 7/52034* (2013.01); *G01S 7/52046* (2013.01); *G01S 7/52085* (2013.01); *G01S 15/8915* (2013.01); *G01S 15/8927* (2013.01); *G01S 15/8993* (2013.01); *G10K 11/346* (2013.01)

(56) References Cited

U.S. PATENT DOCUMENTS

| | | | | |
|---|---|---|---|---|
| 2005/0096538 | A1* | 5/2005 | Chomas | A61B 8/5276 600/437 |
| 2007/0276236 | A1* | 11/2007 | Jong | A61B 8/00 600/437 |
| 2008/0089419 | A1* | 4/2008 | Kervec | G06T 3/4007 375/240.17 |
| 2008/0262354 | A1* | 10/2008 | Yoshida | A61B 8/469 600/443 |
| 2009/0099456 | A1* | 4/2009 | Burcher | A61B 8/00 600/459 |
| 2014/0135625 | A1* | 5/2014 | Konofagou | A61B 8/0883 600/443 |
| 2014/0288876 | A1 | 9/2014 | Donaldson | |
| 2015/0031995 | A1* | 1/2015 | Guracar | A61B 8/5276 600/431 |
| 2015/0272547 | A1* | 10/2015 | Freiburger | A61B 8/485 600/438 |

FOREIGN PATENT DOCUMENTS

| | | |
|---|---|---|
| JP | 2011-024719 A | 2/2011 |
| JP | 2014-050648 A | 3/2014 |
| KR | 2002-0044563 A | 6/2002 |
| KR | 10-2008-0033094 A | 4/2008 |
| KR | 10-2012-0095731 A | 8/2012 |
| KR | 10-2014-0098843 A | 8/2014 |
| KR | 10-2014-0132821 A | 11/2014 |

OTHER PUBLICATIONS

Written Opinion (PCT/ISA/237) dated Sep. 10, 2015 issued by the International Searching Authority in counterpart International Application No. PCT/KR2014/012581.

Communication dated Mar. 8, 2021 issued by the Korean Patent Office in application No. 10-2017-7006745.

Communication dated Sep. 15, 2021 by the Korean Intellectual Property Office in Korean Patent Application No. 10-2017-7006745.

* cited by examiner

353

ULTRASONIC IMAGING DEVICE AND METHOD FOR CONTROLLING SAME

TECHNICAL FIELD

The present disclosure relates to an ultrasound imaging apparatus and a control method of an ultrasound imaging apparatus, which detect motion of a target site and adjust sampling of beamforming according to the motion of a target site.

BACKGROUND ART

An ultrasound imaging apparatus is a device that irradiates an ultrasound signal from a body surface of a subject to a desired part in the body and obtains an image related to a defect of a soft tissue or blood flow by using information of a reflected ultrasound signal (ultrasound echo signal).

Such ultrasound imaging apparatus is compact, inexpensive, and capable of displaying in real time, compared with other imaging apparatuses such as an X-ray probe, an X-ray CT scanner (computerized tomography scanner), an MRI (Magnetic Resonance Image). It is widely used for diagnosis of the heart, the abdomen, urinary organs and in obstetrics because it has high safety because it does not have exposure to radiation.

The ultrasound imaging apparatus includes an ultrasound probe for transmitting an ultrasound signal to an object to obtain an ultrasound image of the object and receiving an ultrasound echo signal reflected from the object.

In addition, the ultrasonic probe includes an acoustic module. Here, the acoustic module includes a transducer for converting an electric signal and an acoustic signal into each other while the piezoelectric material vibrates, and a transducer for reducing the acoustic impedance difference between the transducer and the object so that the ultrasonic waves generated from the transducer can be transmitted to the object as much as possible. A lens layer for converging ultrasonic waves traveling forward of the transducer at specific points, and a sound-absorbing layer for preventing image distortion by blocking the propagation of ultrasonic waves toward the rear of the transducer.

In addition, the ultrasound imaging apparatus can perform beamforming to estimate the size of a reflected wave in a specific space from a plurality of channel data collected by the ultrasonic probe.

Specifically, the beamforming corrects the time difference of the echo signal input through the plurality of transducers, adds a predetermined weight to each echo signal inputted to emphasize the signal at the specific position, or attenuates the signal at the other position relatively so that the echo signal is focused. By the beamforming, the ultrasound imaging apparatus can generate an ultrasound image suitable for grasping the internal structure of the object and display it to the user.

DISCLOSURE

Technical Problem

An object of the present invention is to provide an ultrasound imaging apparatus of matching and synthesizing sampling signals of each group by detecting a motion vector of each group, after dividing the group of the target part and increasing the number of sampling of the beam forming when the group having a lot of motions and decreasing the number of sampling of the beam forming when the group having fewer motions.

Technical Solution

In accordance with one aspect of the present disclosure, an ultrasound imaging apparatus comprising: an ultrasonic probe for transmitting ultrasonic waves to a target object and receiving ultrasonic waves reflected from the object; a beamforming unit for beamforming the received ultrasonic wave and outputting a beamforming signal; a sampling unit for adjusting the number of sampling times of the beamforming signal according to the amount of motion of the object; and an image processing unit for matching and synthesizing the sampled signals.

In accordance with one aspect of the present disclosure, the ultrasound imaging apparatus further comprising, a motion detection unit for dividing the beamforming signals into groups and comparing beamforming signals of one group and the remaining groups to calculate and store motion vectors.

The motion detecting unit may compare a beamforming signal of each group divided for each group with a previous beamforming signal to calculate and store a motion vector.

The sampling unit may adjust a sampling period of the beamforming signal to be less than a predetermined period when the motion vector of the divided group is less than a predetermined value and adjusts a sampling period of the beamforming signal to exceed the predetermined period when the motion vector of the divided group exceeds a preset value.

The sampling unit may adjust a sampling period and a sampling time for each group differently when the motion vectors of the plurality of groups exceed a predetermined value.

The motion detection unit may divide the groups located at the adjacent elevation into different groups.

The image processing unit may interpolate the beamforming signal using linear interpolation, The beamforming signal of the motion sensing unit may be a signal obtained by interpolating a signal.

The image processing unit may interpolate the beamforming signal using linear interpolation, and replaces the sampling signal with the interpolated signal of the same group when the motion vector of the divided group is less than a preset value.

In accordance with one aspect of the present disclosure, a control method for an ultrasound imaging apparatus, the method comprising: transmitting ultrasonic waves to an object, receiving ultrasonic waves reflected from the object; outputting a beamforming signal by beamforming the received ultrasonic waves; sampling the number of times of the beam-forming signal differently according to the amount of motion of the target object; and matching and synthesizing the sampled signals.

In accordance with one aspect of the present disclosure, further comprising,

Dividing the beamforming signal into groups; and calculating and storing a motion vector by comparing the beamforming signals of a group with other groups.

Calculating and storing the motion vector may comprise, calculating and storing a motion vector by comparing the beamforming signal of each group divided by the other groups and the previous beamforming signal.

Sampling the number of times of the beam-forming signal comprises adjusting the sampling period of the beamforming signal to a predetermined period or less, the group having the calculated and stored motion vectors less than a predetermined value and Sampling the group in which the motion vector exceeds a predetermined value is sampled by adjusting the sampling period of the beamforming signal to exceed a predetermined period Sampling the number of times of the beam-forming signal may comprise, sampling by adjusting the sampling period and the sampling time in respective groups in which the motion vector exceeds a predetermined value.

Dividing the beamforming signal into groups may comprise, dividing into different groups located at close elevations.

In accordance with one aspect of the present disclosure, further comprising, interpolating the beamforming signals divided for each group using a linear interpolation method, wherein the beamforming signal divided for each group is supplied to the interpolated signal.

In accordance with one aspect of the present disclosure, further comprising interpolating the beamforming signals divided for each group using a linear interpolation method, wherein matching and synthesizing the signals comprise, replacing the sampling signal of the group having the motion vector equal to or less than the preset value with the interpolated signal of the group having the motion vector equal to or less than a preset value.

Advantageous Effects

According to the ultrasound imaging apparatus and the control method of the ultrasound imaging apparatus described above, it is possible to reduce the distortion of the ultrasound image caused by the motion of the target region in the diagnosis of the target region having different motions by dividing the target portion into a plurality of groups, detecting divided groups the motion vectors, being different the sampling period and sampling time for sampling the beam-forming output signal.

MODE FOR INVENTION

Hereinafter, embodiments of the present invention will be described in detail with reference to the accompanying drawings so that those skilled in the art can easily understand and reproduce the present invention. In the following description, a detailed description of known functions and configurations incorporated herein will be omitted when it may make the subject matter of the present invention rather unclear.

The terms used below are terms selected in consideration of the functions in the embodiments, and the meaning of the terms may vary depending on the user, the intention or custom of the operator, and the like. Therefore, the meaning of terms used in the following embodiments are defined according to their definitions when they are specifically defined below, and when there is no specific definition, they should be construed in a sense generally recognized by ordinary artisans.

In addition, the configurations selectively described below or alternatively described embodiments of the embodiments described in the following description may be combined in a single integrated configuration, if they are not explicitly contradictory to those of ordinary skill in the art.

Hereinafter, an embodiment of an ultrasound imaging apparatus will be described with reference to the accompanying drawings.

Hereinafter, an embodiment in which an ultrasound imaging apparatus is applied to an ultrasound diagnostic system will be described with reference to FIG. 1

Figure 1:
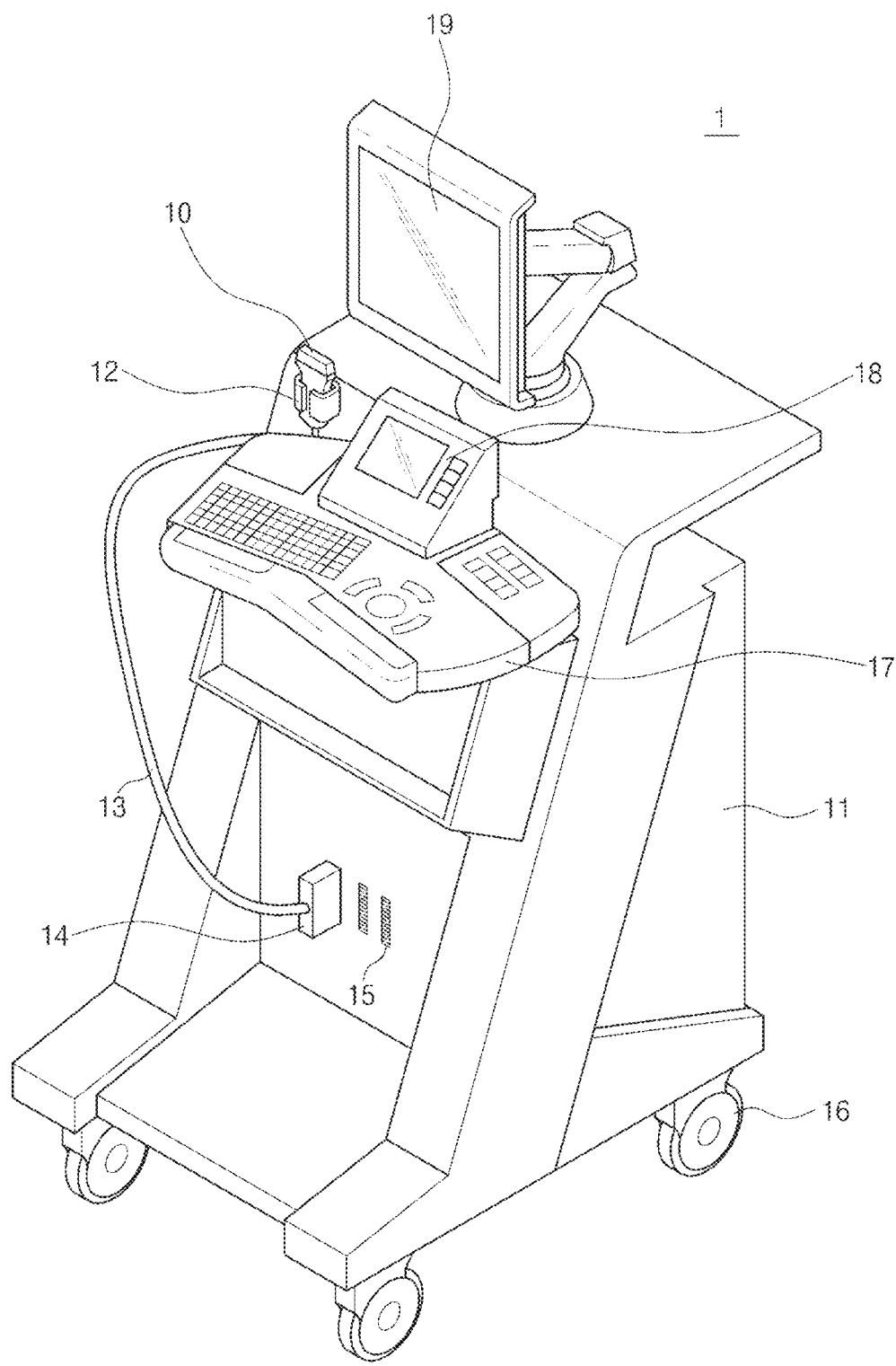
FIG. 1 is a perspective view of an ultrasound diagnostic system to which an ultrasound imaging apparatus according to an embodiment is applied.

FIG. 1 is a perspective view of an ultrasound diagnostic system to which an ultrasound imaging apparatus according to an embodiment is applied.

A main body 11, an ultrasonic probe 10, an input unit 17, a sub display unit 18, and a main display unit 19 is shown in FIG. 1

The main body 11 can receive the transmission signal of of generating unit. When a user inputs an ultrasonic diagnostic command, the transmission signal generating unit may generate a transmission signal and transmit the transmission signal to the ultrasonic probe 10.

At least one female connector 15 may be provided on one side of the main body 11. The female connector 15 may be physically coupled to a male connector 14 connected to a cable 13. The transmission signal generated by the transmission signal generating unit can be transmitted to the ultrasonic probe 10 via the male connector 14 and the cable 13 connected to the female connector 15 of the main body 11.

On the other hand, a plurality of casters 16 for the mobility of the ultrasound diagnostic system 1 may be provided under the main body 11. The plurality of casters 16 can fix the ultrasonic diagnostic system 1 to a specific place or move the ultrasonic diagnostic system 1 in a specific direction.

The ultrasonic probe 10 can transmit or receive ultrasonic waves at a portion contacting the body surface of the object. Specifically, the ultrasound probe 10 converts the generated signal provided from the main body 11 into an ultrasound signal, irradiates the converted ultrasound signal into the body of the target object, and outputs an ultrasound echo signal reflected from a specific part of the target body and transmits it to the main body 11.

To this end, a plurality of acoustic modules for generating ultrasonic waves in accordance with an electrical signal may be provided at one end of the ultrasonic probe 10.

The acoustic module can generate ultrasonic waves according to the applied AC power. Specifically, AC power can be supplied from a power supply unit outside the acoustic module or from an internal power storage device. The transducer of the acoustic module can generate ultrasonic waves by vibrating according to the supplied AC power.

The plurality of acoustic modules may be arrayed in a matrix array, linear array, or convex array. In addition, the plurality of acoustic module may be phased arrays or concave arrays. A cover for covering the acoustic module may be provided on the upper portion of the acoustic module.

The cable 13 is connected to the other end of the ultrasonic probe 10 and the male connector 14 is connected to the end of the cable 13. The male connector 14 can physically engage with the female connector 15 of the main body 11.

The input unit 17 is a part capable of receiving a command related to the operation of the ultrasonic diagnostic system 1. For example, a mode selection command such as an A-mode (Amplitude mode), a B-mode (Brightness mode), a D-mode (Doppler mode), an M-mode (Motion mode) and an ultrasonic diagnostic start command.

The command input through the input unit 17 can be transmitted to the main body 11 by wire or wireless communication.

The input unit 17 may include at least one of a touch pad, a keyboard, a foot switch, and a foot pedal. The touch pad or keyboard may be implemented in hardware and may be located on the top of the main body 11. The keyboard may include at least one of a switch, a key, a wheel, a joystick, a trackball, and a knob. In another example, the keyboard may be implemented in software, such as a graphical user interface. In this case, the keyboard can be displayed through the sub display unit 18 or the main display unit 19. A foot switch or a foot pedal may be provided under the main body 11, and the operator can control the operation of the ultrasound diagnostic system 1 using a foot pedal.

A probe holder 12 for mounting the ultrasonic probe 10 may be provided around the input unit 17. When the ultrasonic diagnostic system 1 is not in use, the user can store the ultrasonic probe 10 in the probe holder 12 for storage. FIG. 1 shows a case where one probe holder 12 is provided in the vicinity of the input unit 17 but the present invention is not limited thereto and the position and the number of the probe holder 12 can be determined by the ultrasonic diagnostic system 1 and may vary widely depending on the overall design or the design or location of some of the components.

The sub display unit 18 may be provided on the main body 11. FIG. 1 shows a case where the sub display unit 18 is provided on the upper part of the input unit 17. The sub display unit 18 may be implemented as a cathode ray tube (CRT), a liquid crystal display (LCD), or the like. The sub display unit 18 can display a menu, an announcement item, and the like necessary for ultrasound diagnosis.

The main display unit 19 may be provided on the main body 11. FIG. 1 shows a case where the main display unit 19 is provided on the sub display unit 18. The main display unit 19 may be implemented as a cathode ray tube or a liquid crystal display. The main display unit 19 can display an ultrasound image obtained in the ultrasound diagnostic process. The ultrasound image displayed through the main display unit 19 may include at least one of a two-dimensional monochrome ultrasound image, a two-dimensional color ultrasound image, a 3D monochrome ultrasound image, and a 3D color ultrasound image.

FIG. 1 illustrates a case where both the sub display unit 18 and the main display unit 19 are provided in the ultrasound diagnostic system 1. However, the sub display unit 18 may be omitted in some cases. In this case, applications and menus displayed through the sub display unit 18 can be displayed through the main display unit 19.

At least one of the sub display unit 18 and the main display unit 19 may be configured to be detachable from the main body 11.

Hereinafter, the configuration and functions of the ultrasound imaging apparatus will be described with reference to FIG. 2

Figure 2:
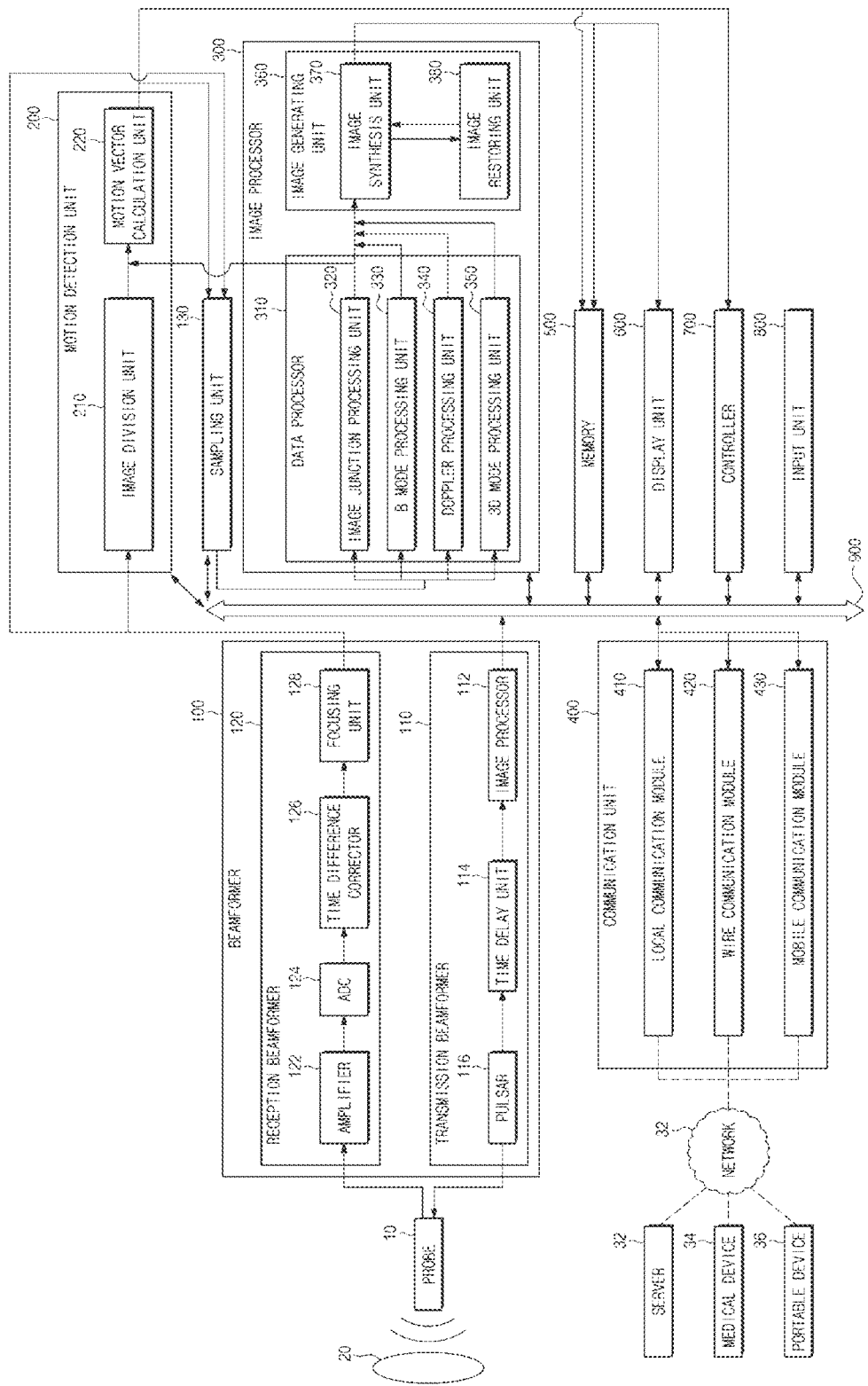
FIG. 2 is a block diagram of a configuration of an ultrasound imaging apparatus according to an embodiment of the present invention.

FIG. 2 is a block diagram of a configuration of an ultrasound imaging apparatus according to an embodiment of the present invention.

As shown in FIG. 2, an ultrasound imaging apparatus 2 includes a ultrasonic probe 10, a beam forming unit 100, a motion sensing unit 200, a sampling unit 130, an image processing unit 300, a communication unit 400, a memory 500, a display unit 600, a control unit 700, and an input unit 800, and the above-described configurations may be connected to each other via a bus 900.

The ultrasound imaging apparatus 2 may be realized not only as a cart type but also as a portable type. Examples of portable ultrasound diagnostic devices include, but are not limited to, a PACS viewer, a smart phone, a laptop computer, a PDA, a tablet PC, and the like.

The probe 10 transmits an ultrasonic signal to an object 20 according to a driving signal applied from the beamforming unit 100 and receives an echo signal reflected from the object 20. The probe 10 includes a plurality of transducers, and the plurality of transducers generate ultrasonic waves that are vibrated in accordance with an electrical signal to be transmitted and have acoustical energy. The probe 10 may be connected to the main body of the ultrasound imaging apparatus 2 in a wired or wireless manner and the ultrasound imaging apparatus 2 may include a plurality of probes 10 according to an embodiment.

A transmission beamformer 110 may supply a driving signal to the probe 10 and may include a transmission signal generating unit 112, a time delay unit 114, and a pulser 116.

The transmission signal generating unit 112 may generate a pulse for forming a transmission ultrasonic wave according to a predetermined pulse repetition frequency (PRF), and the time delay unit 114 may apply time delay to the pulse for determining transmission directionality. Each of the pulses to which the delay time is applied may correspond to a plurality of piezoelectric vibrators included in the probe 10, respectively. In addition, the pulser 116 can apply a driving signal (or a driving pulse) to the probe 10 at a timing corresponding to each pulse to which the delay time is applied.

A reception beamformer 120 may generate ultrasound data by processing the echo signals received from the probe 10 and may include an amplifier 122, an ADC (Analog Digital Converter) 124, a time difference corrector 126 and a focusing unit 128.

The amplifier 122 amplifies the echo signal for each channel and the ADC 124 can analog-to-digital convert the amplified echo signal and the time difference corrector 126 determines the reception directionality. The focusing unit 128 may generate the ultrasound data by summing the echo signals processed by a reception delay unit 166. On the other hand, the reception beamformer 120 may not include the amplifier 122 according to its implementation. That is, when the sensitivity of the probe 10 is improved or the processing bit number of the ADC 124 is improved, the amplifier 122 may be omitted.

The motion sensing unit 200 may receive the beamforming output signals, divide the received signals, and calculate a motion vector. The motion detection unit 200 may include a division unit 210 and a motion vector calculation unit 220.

The division unit 210 receives the beamforming output signal output from the focusing unit 128 of the reception beamformer and divides the beamforming output signal into a plurality of groups. The division unit 210 may divide a motion into a portion having a strong motion and a portion not having a motion according to a previously detected motion vector, or may divide the group into a number of divisions to be set in advance or inputted by the user.

The motion vector calculation unit 220 may calculate the motion vectors of the beamforming output signals of the plurality of divided groups. For example, the motion vector calculation unit 220 may calculate a motion vector by cross-correlating a currently output beamforming signal of a group with a beamforming signal of the remaining group. In addition, the motion vector calculation unit 220 may calculate a motion vector by cross-correlating the currently output beamforming signal with the previously output beamforming signal. When a motion vector is calculated by cross-correlating beamforming signals, the lower the value, the more severe the motion, and the higher the value, the lower the motion. However, the calculation of the motion vector by the motion vector calculation unit 220 is not limited to the calculation of the motion vector by comparison with the previous beamforming signal through cross correlation.

The sampling unit 130 may change the sampling of the beam forming output signal according to the motion of the target site. Specifically, the motion vector calculated by the motion vector calculation unit 220 may be analyzed to sample the beamforming output signal by increasing the sampling period of the group having a lot of motion and making the sampling period of the group having a small motion slower.

The image processing unit 300 may generate and display an ultrasound image through a scan conversion process on the ultrasound data generated by the sampling unit 130. On the other hand, the ultrasound image can be used for a gray scale image and a 3D image obtained by scanning an object in an A mode (amplitude mode), a B mode (brightness mode) and an M mode (motion mode). Doppler images representing moving objects may be included using the Doppler effect. The Doppler image may include a blood flow Doppler image (also referred to as a color Doppler image) representing blood flow, a tissue Doppler image representing tissue movement, and a spectral Doppler image representing a moving velocity of the object as a waveform.

The image processing unit 300 may include a data processing unit 310 and an image generating unit 360.

The data processing unit 310 may include an image matching processing unit 320, a 3D mode processing unit 350, a B mode processing unit 330, and a D mode processing unit 340.

The image matching processing unit 320 can estimate an image through linear interpolation for a time period during which the motion is not sampled in a group having a small number of motions during a period in which the motion is sampled by a group having a large number of motions. The interval can be estimated by interpolation.

In addition, the image matching processing unit 320 may substitute the estimated beamforming signals into a time domain in which the sampled beamforming signals are not sampled, and match the continuous signals. The image matching processing unit 320 may also assist in calculating a motion vector by transmitting a signal obtained by linearly interpolating the beamforming signal to a motion vector calculating unit and comparing the linear interpolated signal with a previous interpolated signal.

In addition, the 3D mode processing unit 350 may analyze the output signals of different depths and heights output from the beamforming unit to generate a 3D volume, and perform rendering to combine the 3D volume.

In addition, the B mode processing unit 330 can extract the B mode component from the ultrasonic data and process it. The image generating unit 360 may generate an ultrasound image in which the intensity of the signal is expressed by the brightness based on the B mode component extracted by the B mode processing unit 330.

The D mode processing unit 340 extracts a Doppler component from the ultrasound data, and the image generating unit 360 can generate a Doppler image that expresses the motion of the object in color or waveform based on the extracted Doppler component.

The image generating unit 360 may generate an ultrasound image by temporally or spatially combining data processed by the data processing unit 310.

The image generating unit 360 may include an image combining unit 370 and an image restoring unit 380.

The image combining unit 370 may synthesize the temporally or spatially divided sampled beamforming output signals into an ultrasound image after being subjected to image matching processing and then synthesized temporally or spatially.

In addition, the image restoring unit 380 may reconstruct the distorted ultrasound image signal using an estimation function or an interpolation function for a data processing process, a diagnostic process, or other processes.

In addition, the image generating unit 360 may generate an elastic image that images the degree of deformation of the object 20 according to the pressure. Furthermore, the image generating unit 360 may display various additional information on the ultrasound image in text or graphics. Meanwhile, the generated ultrasound image may be stored in a memory 500.

The communication unit 400 may be connected to the network 30 by wire or wireless, and may communicate with an external device or a server. The communication unit 400 can exchange data with other medical devices in a hospital server or a hospital connected through a PACS (Picture Archiving and Communication System). In addition, the communication unit 400 can perform data communication according to a DICOM (Digital Imaging and Communications in Medicine) standard.

The communication unit 400 can transmit and receive data related to diagnosis of a target object such as ultrasound image, ultrasound data, and Doppler data of the object 20 through the network 30. A medical image can also be transmitted and received. Further, the communication unit 400 may receive information on the diagnosis history of the patient, the treatment schedule, and the like from the server and use the diagnosis information in the diagnosis of the target object 20. Further, the communication unit 400 may perform data communication with not only a server or a medical device in a hospital but also with a doctor or a portable terminal of a patient.

The communication unit 400 may be connected to the network 30 by wire or wireless and may exchange data with a server 32, a medical device 34, or a portable terminal 36. The communication unit 400 may include one or more components that enable communication with an external device. For example, a short range communication module 410, a wired communication module 420, and a mobile communication module 430.

The short range communication module 410 may be a module for short range communication within a predetermined distance. The local communication technology according to an exemplary embodiment of the present invention may include a wireless LAN, Wi-Fi, Bluetooth, ZigBee, Wi-Fi Direct, an ultra-wideband (UWB) IrDA, Infrared Data Association), BLE (Bluetooth Low Energy), NFC (Near Field Communication), and the like.

The wired communication module 420 refers to a module for communication using an electrical signal or an optical signal. In the wired communication technology according to an exemplary embodiment, a pair cable, a coaxial cable, an optical fiber cable, and an ethernet cable may be included.

The mobile communication module 430 may transmit and receive a radio signal to at least one of a base station, an external terminal, and a server on a mobile communication network. The wireless signal may include various types of data depending on a voice call signal, a video call signal or a text/multimedia message transmission/reception.

The memory 400 may store various types of information processed in the ultrasound imaging apparatus 2. For example, the memory 400 may store medical data related to diagnosis of a target object such as input/output ultrasound data and ultrasound images, and may store an algorithm or a program executed in the ultrasound imaging device 2.

The memory 400 may be implemented by various types of storage media such as a flash memory, a hard disk, and an EEPROM. Also, the ultrasound imaging apparatus 2 may operate a web storage or a cloud server that performs a storage function of the memory 400 on the web.

The display unit 600 can display and output the generated ultrasound image. The display unit 600 may display various information processed in the ultrasound imaging device 2 on the screen through a GUI (Graphic User Interface) as well as an ultrasound image. Meanwhile, the ultrasound imaging apparatus 2 may include two or more display units 600 according to an embodiment.

The control unit 700 can control the operation of the ultrasound imaging apparatus 2 as a whole. That is, the control unit 700 includes the probe 10, the beamforming unit 100, the motion sensing unit 200, the sampling unit 130, the image processing unit 300, the communication unit 400, the memory 500, the display unit 600 and the input unit 800.

The input unit 800 may be means for receiving data for controlling the ultrasound imaging apparatus 2 from a user. The input unit 800 may include a hardware configuration such as a keypad, a mouse, a touch panel, a touch screen, a trackball, a jog switch, and the like. The input unit 800 may include an electrocardiogram measurement module, a breath measurement module, a fingerprint recognition sensor, an iris recognition sensor, a depth sensor, a distance sensor, and the like.

Some or all of the probe 10, the beamforming unit 100, the image processing unit 300, the communication unit 400, the memory 400, the input unit 800, and the control unit 700 may be operated by a software module. The present invention is not limited thereto, and some of the above-described configurations may be operated by hardware. At least some of the beamforming unit 100, the image processing unit 300, and the communication unit 400 may be included in the control unit 700, but the present invention is not limited to this embodiment.

Hereinafter, an embodiment of an ultrasonic probe for emitting an ultrasonic signal and receiving an echo signal reflected from a target site will be described with reference to FIG. 3.

Figure 3:
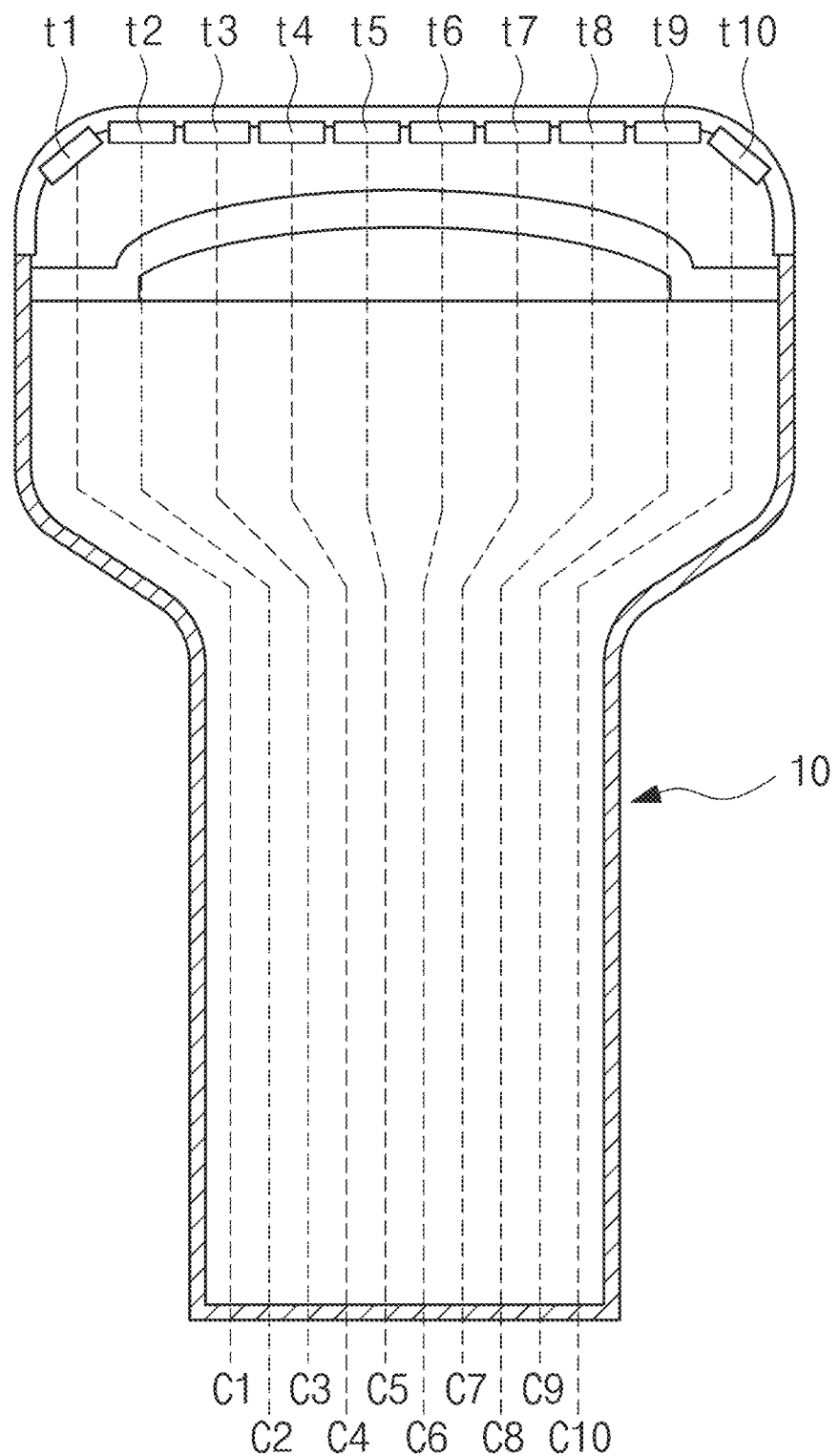
FIG. 3 is a cross-sectional view of a plurality of transducer arrays corresponding to a plurality of channels in an ultrasonic probe according to an embodiment.

FIG. 3 is a cross-sectional view of a plurality of transducer arrays corresponding to a plurality of channels in the ultrasonic probe according to the present invention. The ultrasound imaging apparatus may include an ultrasound probe 10, and the ultrasound probe 10 may collect information about a target site using ultrasound. At this time, the ultrasonic probe 10 may be a structure capable of detecting a 3D volume.

The ultrasonic probe 10 may include a plurality of ultrasonic probes 10 arranged in a matrix. A plurality of transducers arranged in a matrix form can output a plurality of echo signals, and the output echo signals can be accumulated to generate a 3D volume.

In addition, the ultrasonic probe 10 may include a transducer arranged in a row and a structure for moving a transducer arranged in a row.

More specifically, rails may be provided at both ends of a plurality of transducers arranged in a line, in a direction perpendicular to the direction in which a plurality of transducers are arranged.

The ultrasonic probe 10 can acquire a plurality of echo signals by moving a plurality of transducers arranged in a row in a scanning direction along the rails and create a 3D volume by accumulating the obtained plurality of echo signals Hereinafter, for convenience of explanation, it is assumed that the ultrasonic probe 10 arranges the transducers in a matrix form.

Referring to FIG. 3, the ultrasonic probe 10 may have a plurality of ultrasonic transducers (t1 to t10) at one end thereof. The ultrasonic transducers (t1 to t10) generate corresponding ultrasonic waves according to an applied signal or a power source, irradiate the ultrasonic waves to a target object, receive echo ultrasonic waves reflected from the object, and generate and output an echo signal.

Specifically, the ultrasonic transducers (t1 to t10) are supplied with power from an external power supply device or an internal power storage device such as a battery, and are driven by the ultrasonic transducers (t1 to t10). The ultrasonic waves can be generated by the ultrasonic transducers In addition, the ultrasonic transducer (p10) generates an alternating current having a frequency corresponding to the vibration frequency while the piezoelectric material or the thin film vibrates according to the reception of the ultrasonic wave, thereby converting the ultrasonic wave into the echo signal.

Then, the generated echo signal can be transmitted to the main body through the plurality of channels (c1 to c10).

The ultrasonic transducers (t1 to t10) described above include a magnetostrictive ultrasonic transducer using a magnetostrictive effect of a magnetic material, a piezoelectric ultrasonic transducer using a piezoelectric effect of a piezoelectric material, Capacitive micromachined ultrasonic transducer (cMUT) for transmitting and receiving ultrasonic waves using vibration of a micromachined hundreds or thousands thin films.

In addition, other types of transducers capable of generating an ultrasonic wave in accordance with an electrical signal or generating an electric signal in accordance with an ultrasonic wave may also be used as an example of the ultrasonic transducers t1 to t10 described above.

Hereinafter, one embodiment of a beamforming unit including a transmission beamformer and a reception beamformer will be described with reference to FIG. 4 and FIG. 5

The beamforming unit 100 may include a transmission beamformer 110 and a reception beamformer 120.

Figure 4:
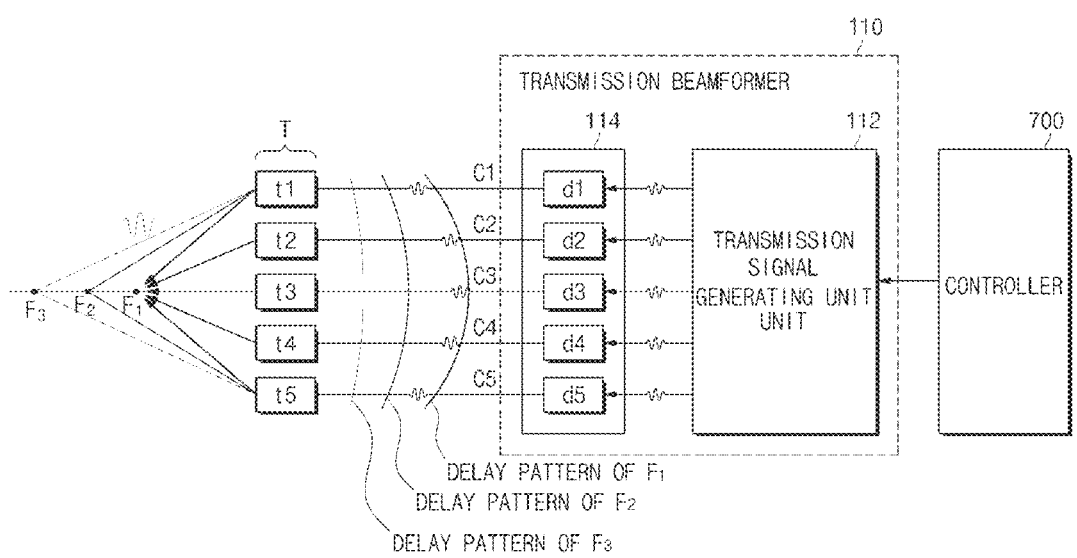
FIG. 4 is a block diagram illustrating a configuration of a transmission beamformer.

FIG. 4 is a block diagram illustrating a configuration of a transmission beamformer.

The transmission beamformer 110 may perform transmit beamforming using the transmission signal generating unit 112 and a time delay unit 114. The transmission beamforming refers to focusing ultrasound generated from at least one transducer (T) at a focal point. That is, ultrasonic waves are generated in the transducer (T) by appropriately ordering the ultrasonic waves generated from at least one transducer (T) in order to overcome the time difference in reaching the focus.

Specifically, the transmission signal generating unit 112 of the transmission beamformer 110 can generate a transmission signal to at least one transducer (T) in accordance with the control signal of a control unit 700. At this time, the transmission signal may be generated in a form of high-frequency alternating current corresponding to the number of transducers. The transmission signal generated by the transmission signal generating unit 112 may be transmitted to the time delay unit 114.

The time delay unit 114 may apply a time delay to each transmission signal to adjust the time to reach the corresponding transducer (T). When a transmission signal delayed by the time delay unit 114 is applied to the transducer (T), the transducer (T) generates an ultrasonic wave corresponding to the frequency of the transmission signal. The ultrasonic waves generated in each transducer (T) are focused at a focal point. The position of the focal point at which the ultrasonic waves generated in the transducer (T) converges may vary depending on what type of delay pattern is applied to the transmission signal.

FIG. 4 illustrates five transducers (t1 to t5), and three delay patterns that can be applied to the transmission signals are illustrated by a thick solid line, a medium-thick solid line, and a thin solid line.

For example, when a delay pattern of the same shape as a thick solid line is applied to the transmission signals generated in the transmission signal generating unit 112, the ultrasonic waves generated in the respective transducers (t1 to t5) are transmitted to the first focal point (F1)

When applying a delay pattern of the same shape as a medium-thick solid line to each of the transmission signals generated by the transmission signal generation unit 112, the ultrasonic waves generated in the respective transducers (t1 to t5) are transmitted to the second focus (F2) farther than the first focus (F1).

When a delay pattern of the same shape as a thin solid line is applied to each transmission signal generated in the transmission signal generation unit 112, the ultrasonic waves generated in the respective transducers (t1 to t5) can be focused at the (F3) farther then the second focus (F2).

That is, the position of the focal point can be changed according to the delay pattern applied to the transmission signal generated by the transmission signal generating unit 112. In the case of applying only one delay pattern, the ultrasonic waves irradiated to the object may be fixed-focused at a fixed focus, but in the case of applying another delay pattern, the ultrasonic waves irradiated to the object may be multi-focused.

Thus, the ultrasonic waves generated in each transducer (T) may be fixedly focused at one point, or may be focused at multiple points. The ultrasonic waves irradiated to the inside of the object are reflected at the target site in the object, and the reflected echo ultrasonic waves can be received by the transducer (T). The transducer (T) can convert the received echo ultrasonic wave into an electric signal and output it. The signal output from the transducer (T) may be amplified and filtered and then converted into a digital signal and provided to the reception beamformer 120.

Figure 5:
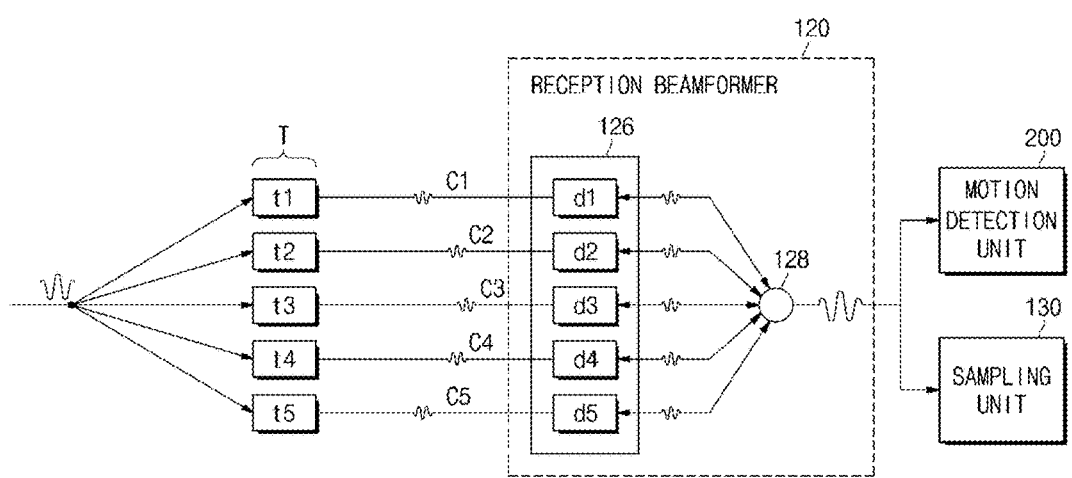
FIG. 5 is a block diagram illustrating the configuration of a reception beamformer.

FIG. 5 is a block diagram illustrating the configuration of a reception beamformer. The reception beamformer 120 may include a time difference corrector 126 and a focusing unit 128 to perform reception beamforming on the received signal (S) converted into a digital signal. The reception beamforming is to correct the parallax existing between the reception signals (S) output from the respective transducers (T) and to focus them.

Specifically, the time difference corrector 126 transmits the received signals to the focusing unit 128 at the same time by delaying the received signals (S) output from the respective transducers (T) by a predetermined time. The focusing unit 128 can focus the received signals (S) whose time differences are corrected by the time difference corrector 126 into one. The focusing unit 128 may add a predetermined weighting factor, for example, a beamforming coefficient to each received signal to emphasize or attenuate the predetermined received signal (S), as compared to other received signals. The focused received signal (S) may be provided to the motion sensing unit 200 and the sampling unit 130.

Hereinafter, referring to FIGS. 6 to 10, a motion detecting unit divides a target portion into a plurality of groups, detects a motion vector of each group, and samples a beamforming output signal according to a motion vector of the sampling unit.

The dividing unit can divide the target region into a plurality of groups and assign a unique identification number. The dividing unit may divide the target part into a plurality of groups by the number of divisions stored in advance in the memory, or may divide the target part into a plurality of groups by the number of divisions input by the user through the input unit.

In addition, the dividing unit may divide the target region into a plurality of groups by grouping the regions of the target region having similar motion vectors on the basis of the previously calculated motion vectors. In addition, various methods for dividing the target portion into a plurality of groups and calculating motion vectors for each group may be used as an example of the divided portion.

The motion vector calculation unit may calculate a motion vector for each group by using a beamforming output signal of a plurality of groups or a signal obtained by interpolating a sampling signal.

For example, the motion vector calculator may compare the interpolation signal of one group with the interpolation signal of the remaining group to determine the amount of motion of the target part. An example of calculating the motion vector can be expressed by the following equation (1).

$$m(p\_r) = \min\left(\frac{L\_r'(p\_r, t\_r) * L\_n'(p\_n, t\_n)}{|L\_r'(p\_r, t\_r)| \cdot |L\_n'(p\_n, t\_n)|}\right)$$ [Math FIG. 1]

Equation (1) is a formula for calculating a group of motion vectors.

T_r is the sampling time of one group, L_r (p_r, t_r) is a group of sampling signals, L_r'(p_r, t_r) is a signal obtained by interpolating a group of sampling signals, p_n is an n-th group of pixels, t_n is the sampling point of the n-th group, L_n (p_n, t_n) is an n-th group of sampling signals, L_n'(p_n, t_n) is a signal obtained by interpolating the sampling signal of the nth group, * is a cross-correlation operator, and · is an operator of multiplication.

The motion vector calculator calculates an absolute value of L_r'(p_r, t_r) by a cross-correlation between a signal L_r'(p_r, t_r) obtained by interpolating the sampling signal of one group and a signal L_1'(p_1, t_1) obtained by interpolating the sampling signal of the first group among the remaining groups. The absolute value of L_1'(p_1, t_1) is multiplied, and the first result value is calculated.

Then, the motion vector calculator calculates the n-th result value by calculating up to the n-th group as in the above method, and determines the smallest result value among the first to n-th result values as a group of motion vectors.

The motion detection unit can detect a motion of a target region by calculating a motion vector of one group using the motion vector calculation equation as shown in Equation (1).

In another example, the motion vector calculator may determine the amount of motion of a target portion by comparing a current group of interpolation signals with a previous group of interpolation signals. An example of calculating the motion vector can be expressed by the following equation (2).

$$m(p\_r) = \min\left(\frac{L\_r'(p\_r, t\_r) * L\_p'(p\_p, t\_p)}{|L\_r'(p\_r, t\_r)| \cdot |L\_p'(p\_p, t\_p)|}\right)$$ [Math FIG. 2]

Equation (2) is a formula for calculating a group of motion vectors. T_r is the sampling time of one group, L_r (p_r, t_r) is a group of sampling signals, L_r'(p_r, t_r) is a signal obtained by interpolating a group of sampling signals, p_n is an n-th group of pixels, t_n is the sampling point of the n-th group, L_n (p_n, t_n) is an n-th group of sampling signals, L_n'(p_n, t_n) is a signal obtained by interpolating the sampling signal of the nth group, * is a cross-correlation operator, and · is an operator of multiplication.

The motion vector calculator calculates the absolute value of L_r'(p_r, t_r) and the absolute value of L_p'(p_p, t_p) by cross-correlating L_r'(p_r, t_r), which is a signal obtained by interpolating a sampling signal of one group with a sampling signal of L_r'(p_r, t_r), and a matrix of a motion vector of a group is calculated.

Thereafter, the motion vector calculator may determine a matrix having the smallest value among the matrixes related to the motion vector as the motion vectors of the current group. Then, the motion vector calculating unit may calculate the motion vectors of other groups through the same calculation for other groups.

The motion detection unit can detect a motion of a target region by calculating a motion vector of one group using the motion vector calculating equation as shown in Equation (2).

The motion vector calculated by the above-mentioned method can be transmitted to the memory, the control unit, and the sampling unit.

Hereinafter, an embodiment in which the beamforming output signal is sampled by the sampling unit on the basis of the motion vector calculated by the motion vector calculating unit will be described.

Figure 6:
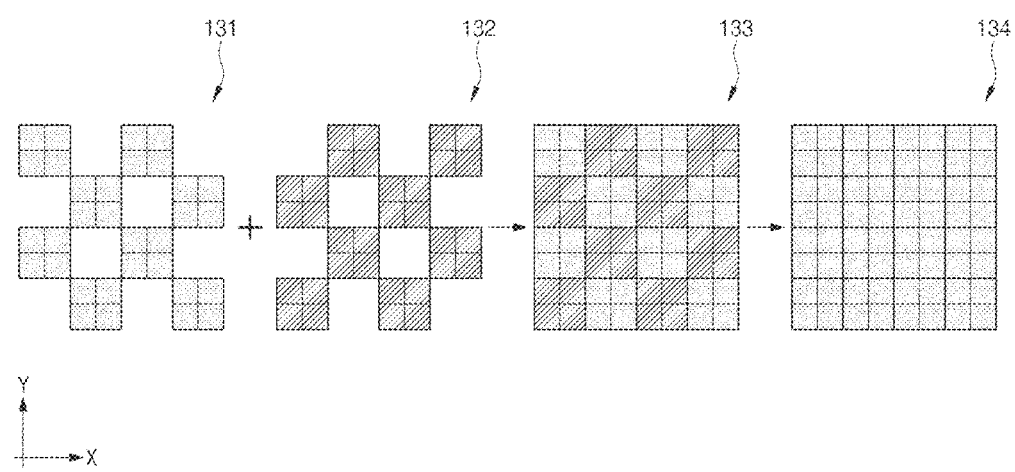
FIG. 6 is a conceptual diagram for matching and combining sampling signals by differentiating sampling of a beamforming output signal for each group according to an embodiment.

FIG. 6 is a conceptual diagram for matching and combining the sampling signals by differentiating the sampling of the beam-forming output signal for each group.

The sampling unit may increase the sampling period of a group 131 having a small motion based on the motion vector to a range exceeding a predetermined period. Therefore, when sampling the group 131 having a small amount of motion, the sampling unit can sample the beamforming signal with a small sampling frequency.

On the other hand, the sampling unit may reduce the sampling period of a motion-rich group 132 to a predetermined period or less based on the motion vector. Accordingly, when sampling the motion-rich group 132, the sampling unit may frequently adjust the sampling frequency to sample the beamforming signal.

The predetermined motion vector and the predetermined sampling period of the sampling unit may be values input by the user through the input unit or values stored in the memory. In addition, various values for reducing the distortion of the ultrasound image due to the motion of the target portion may be used as an example of a preset motion vector of the sampling unit and a predetermined sampling period.

As shown in FIG. 6, the image generating unit generates a single ultrasound full image 133 by combining the sampling signals of the group 131 having a small motion and the sampling signals of the motion-rich group 132 having a lot of motion. A final ultrasound full image 134 can be generated by spatially synthesizing the video signals through matching.

Figure 7A:
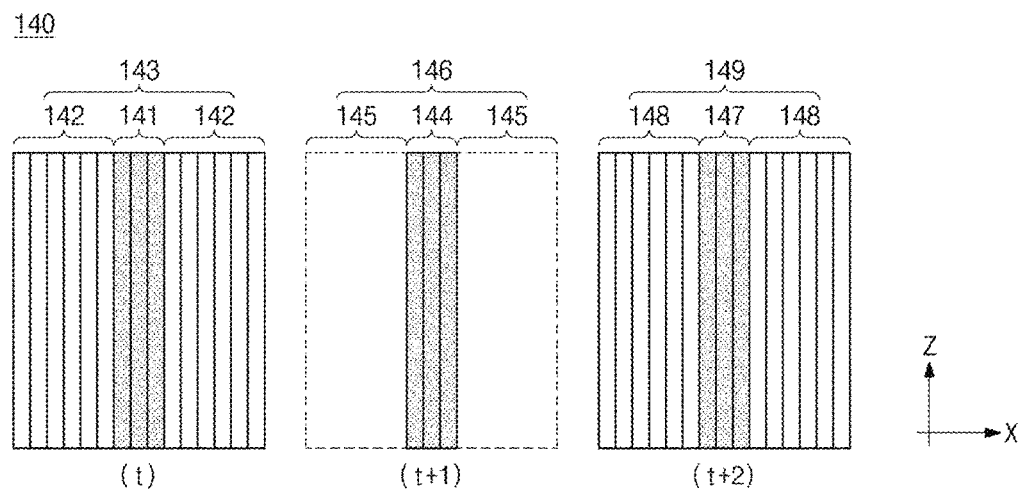
FIG. 7A is a conceptual diagram for sampling a beamforming output signal according to an embodiment so as to have a different period for each group.
Figure 7B:
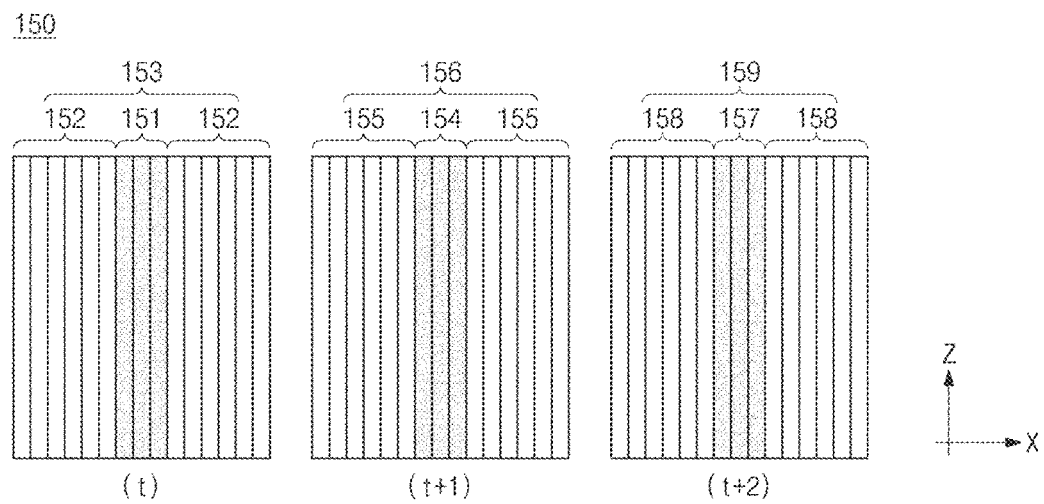
FIG. 7B is a conceptual diagram for interpolating a beamforming output signal sampled to have a different period for each group according to an embodiment.
Figure 7C:
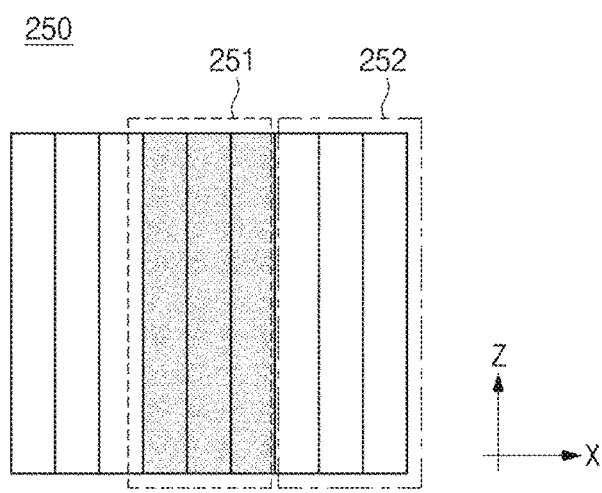
FIG. 7C is a conceptual diagram for synthesizing interpolated sampling signals according to an embodiment.

FIG. 7A is a conceptual diagram for sampling the beamforming output signal so as to have a different period for each group, FIG. 7B is a conceptual diagram for interpolating such that the beamforming output signal is sampled so as to have a different period for each group and FIG. 7C is a conceptual diagram for synthesizing the interpolated sampling signal.

As shown in FIG. 7A, the sampling unit simultaneously samples the beam-forming output signals of a group 141 having a lot of motion and a group 142 having a small motion at a time t. It is possible to sample an ultrasound image signal 143 for the z-axis which is the axial direction of the site.

Then, the sampling unit samples only the beam-forming output signal of a group 144 having a large motion at time t+1, and does not perform the sampling of the beam-forming output signal of a group 145 having a small motion. Therefore, it is possible to sample an ultrasound image signal 146 with respect to the x-axis, which is the lateral side of only the group 144 having a lot of motions, and the z-axis, which is the axial direction of the target region.

Finally, the sampling unit can simultaneously sample the beamforming output signals of a group 147 having a lot of motion and a group 148 having a small motion at a time t+2. The sampling unit can sample an ultrasound image signal 149 about the x-axis, which is the lateral side of the target region, and the z-axis, which is the axial direction of the target region. Then, as shown in FIG. 7B, the image processor outputs to an ultrasound image signal 153 by spatial matching the beamforming signals of a group 151 having a lot of motion and a group 152 having a small motion at a time t. Also, the image processing unit can perform only spatial matching and output an ultrasound image signal 159 obtained by sampling all of the beam forming output signals of a group 157 having a lot of motion and a group 158 having a small motion at time t+2.

However, since the sampling unit has not been sampled for the group 145 having a small motion at the time t+1, the image processing unit matches the beamforming output signal of a group 155 with a small motion through temporal matching on the basis of the sampling signal of the groups 142, 148 with low motion at time t and at time t+2. Thereafter, the image processing unit can output the signals of the group 155 having a small motion and the sampling signals of the group 154 having a large number of motions as a single ultrasound image signal 156 through spatial matching. Accordingly, as shown in FIG. 7C, one ultrasound image signal 250 is acquired through temporal or spatial matching and synthesis of the ultrasound image signals of a group 251 having a lot of motion and a group 252 having a small motion.

Figure 8A:
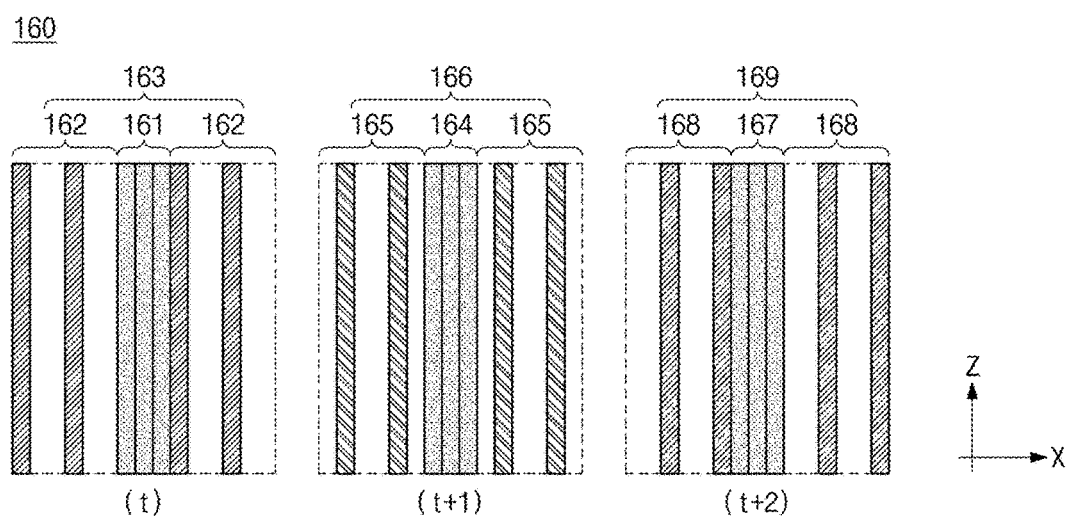
FIG. 8A is a conceptual diagram for sampling a beamforming output signal according to an embodiment so as to have a different period and time for each group.
Figure 8B:
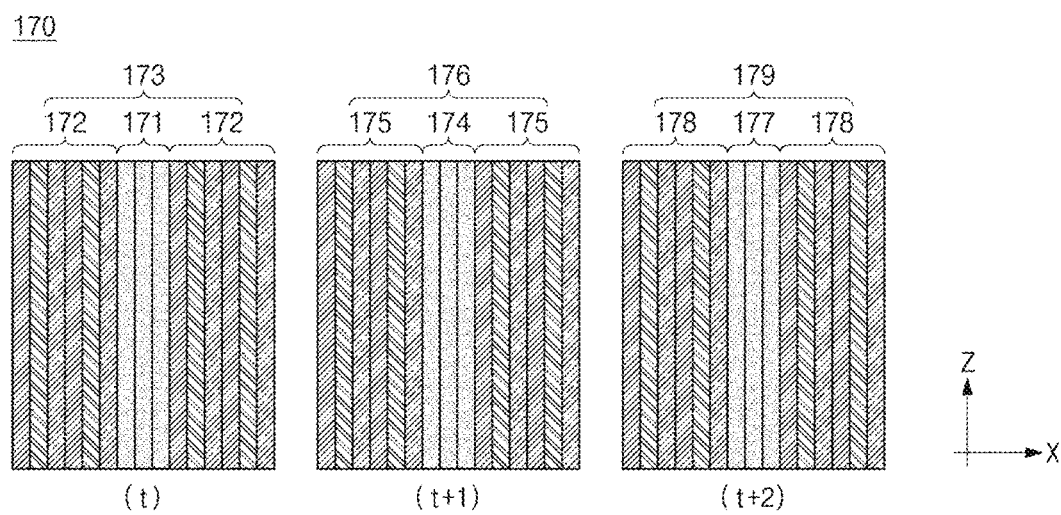
FIG. 8B is a conceptual diagram for interpolating a beamforming output signal sampled so as to have a different period and time for each group according to an embodiment.
Figure 8C:
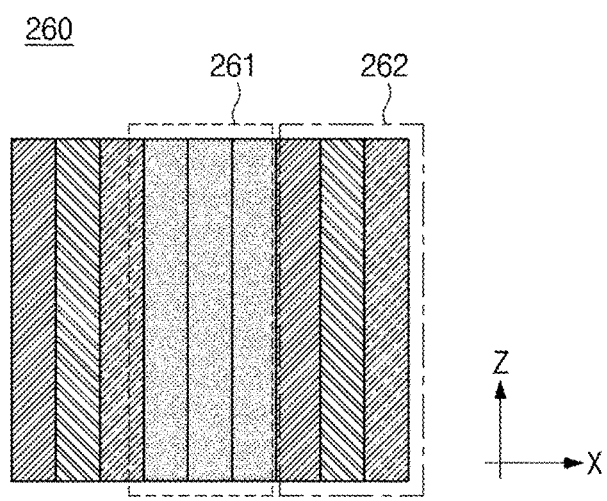
FIG. 8C is a conceptual diagram for synthesizing interpolated sampling signals according to an embodiment.

FIG. 8A is a conceptual diagram for sampling a beam-forming output signal so as to have different periods and time points for each group, FIG. 8B is a conceptual diagram for interpolating a beamforming output signal sampled so as to have different periods and time points for each group and FIG. 8C is a conceptual diagram for synthesizing the interpolated sampling signal.

As shown in FIG. 8A, the motion detection unit divides the target region into four groups, calculates the motion vectors of the four groups, and calculates the motion vectors of the target region as the motion vectors of a motion vector group 161 and the first group, the second group and the third group.

Thereafter, the sampling unit simultaneously samples the beamforming output signals of a first group 162 having a large motion and the first group 162 having a large number of motions at a time t, and outputs the x-axis, which is the lateral direction of the target region. An ultrasound image signal 163 for the z-axis, which is the axial direction, can be sampled.

Then, the sampling unit simultaneously samples the beam-forming output signals of a group 164 having a lot of motion and a second group 165 having a small motion at a time t+1. It is possible to sample an ultrasound image signal 166 for the z-axis which is the axial direction.

Finally, the sampling unit simultaneously samples the beamforming output signals of a third group 167 and a low motion group 168, which have a lot of motions at time t+2. An ultrasonic image signal 169 for the z-axis, which is the axial direction of the ultrasonic image 169, can be sampled.

However, since the sampling unit does not consecutively sample three groups with small motions at time t, time t+1, and time t+2, the image processing unit performs sampling at time t, time t+1, time t+2. A first group 172, a second group 175, and a third group 178 are sampled only once.

Therefore, as shown in FIG. 8B, the image processing unit matches the beamforming small motions of groups 172, 175, 178 based on temporal matching the sampling signals of the first group 172, the second group 175, and the third group 178.

The image processing unit may output one ultrasound image signal 173, 176, 179 by spatially matching the signals of the groups 172, 175, 178 having a small temporally matched motion and the sampling signals of groups 171, 174, and 177 having a lot of motions. Therefore, as shown in FIG. 8C, the image processing unit may obtain an ultrasound image signal 260 processed through temporal or spatial matching and synthesis of an ultrasound image signal of a group 261 having a lot of motions and a group 262 having a lot of motions can be obtained.

Figure 9A:
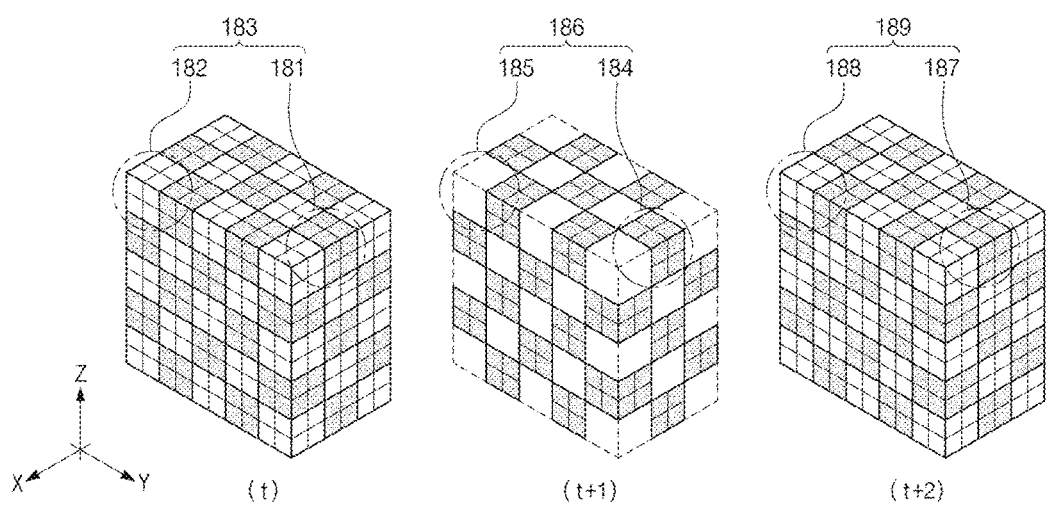
FIG. 9A is a conceptual diagram for sampling a beamforming output signal so that groups of adjacent heights have different periods according to an embodiment.
Figure 9B:
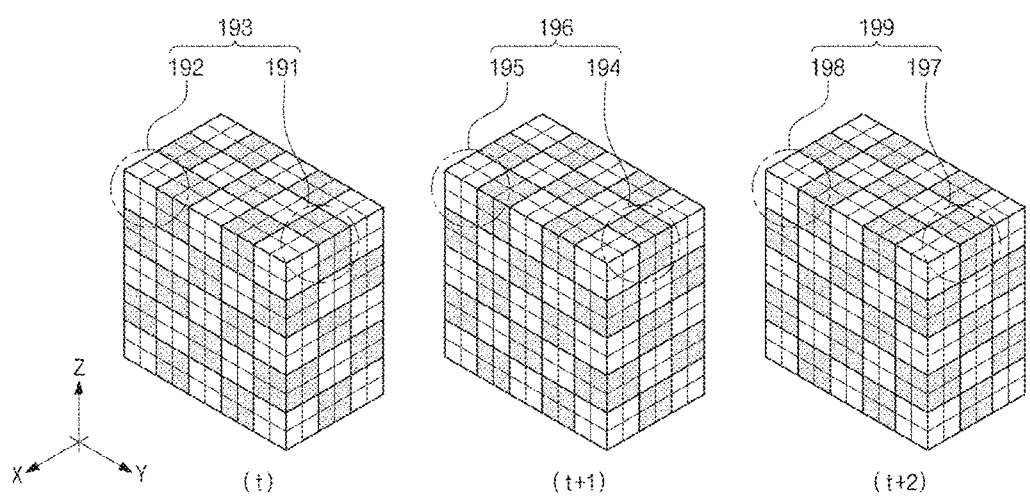
FIG. 9B is a conceptual diagram for interpolating the sampling of the beamforming output signal so that groups of adjacent heights have different periods according to an embodiment.

FIG. 9A is a conceptual diagram for sampling a beam-forming output signal so that groups of adjacent heights have different periods, and FIG. 9B is a conceptual diagram for the concept of interpolating the sampling of the beam-forming output signal so that groups of adjacent heights have different periods.

As shown in FIG. 9A, the sampling unit can simultaneously sample the beam-forming output signal of the group 181 having a lot of motion and the group 182 having a small motion at a time t. The sampling unit can sample the ultrasound image signal 183 for the x-axis which is the lateral side of the target site, the y-axis which is the height direction of the target site (Elevation) and the z-axis which is the axial direction of the target site.

In this case, the sampling unit can sample the beam-forming output signal by dividing adjacent groups on the y-axis, which is the height direction (Elevation) of the target site, into different groups.

Then, the sampling unit samples only the beam-forming output signal of a group 184 having a large motion at the time t+1, and does not perform the sampling of the beam-forming output signal of a group 185 having a small motion.

Therefore, the sampling unit may sample an ultrasound image signal 186 about the x-axis, the y-axis, the height direction of the target region, and the z-axis, which is the axial direction of the target region. The sampling unit can sample an ultrasound image signal 189 for the x-axis which is the lateral side of the target portion, the y-axis which is the height direction of the target portion (Elevation) and the z-axis which is the axial direction of the target portion (Axial)

At the time t+2, the beamforming output signals of a group 187 having a lot of motion and a group 188 having a small motion are simultaneously sampled. Thereafter, as shown in FIG. 9B, the image processing unit can output an ultrasound image signal 193 obtained by sampling all the beam-forming output signals of a group 191 having a lot of motion and a group 192 having a small motion by performing only spatial matching at time t.

Also, the image processing unit can output an ultrasound image signal 199 obtained by sampling all beamforming output signals of a motion group 197 and a low motion group 198, by performing only spatial matching at time t+2.

However, since the sampling unit has not sampled the group 185 having a small motion at the time t+1, the image processing unit matches the beamforming output signals of a group 195 with a small motion through temporal matching based on the sampling signals of the groups 182 and 188 having a small motion at time t and time t+2.

Thereafter, the image processing unit can output one ultrasound image signal 196 by the spatial matching sampling signal of the signal of the group 185 having a small motion and the signal of a group 194 having a large number of motions.

Figure 10A:
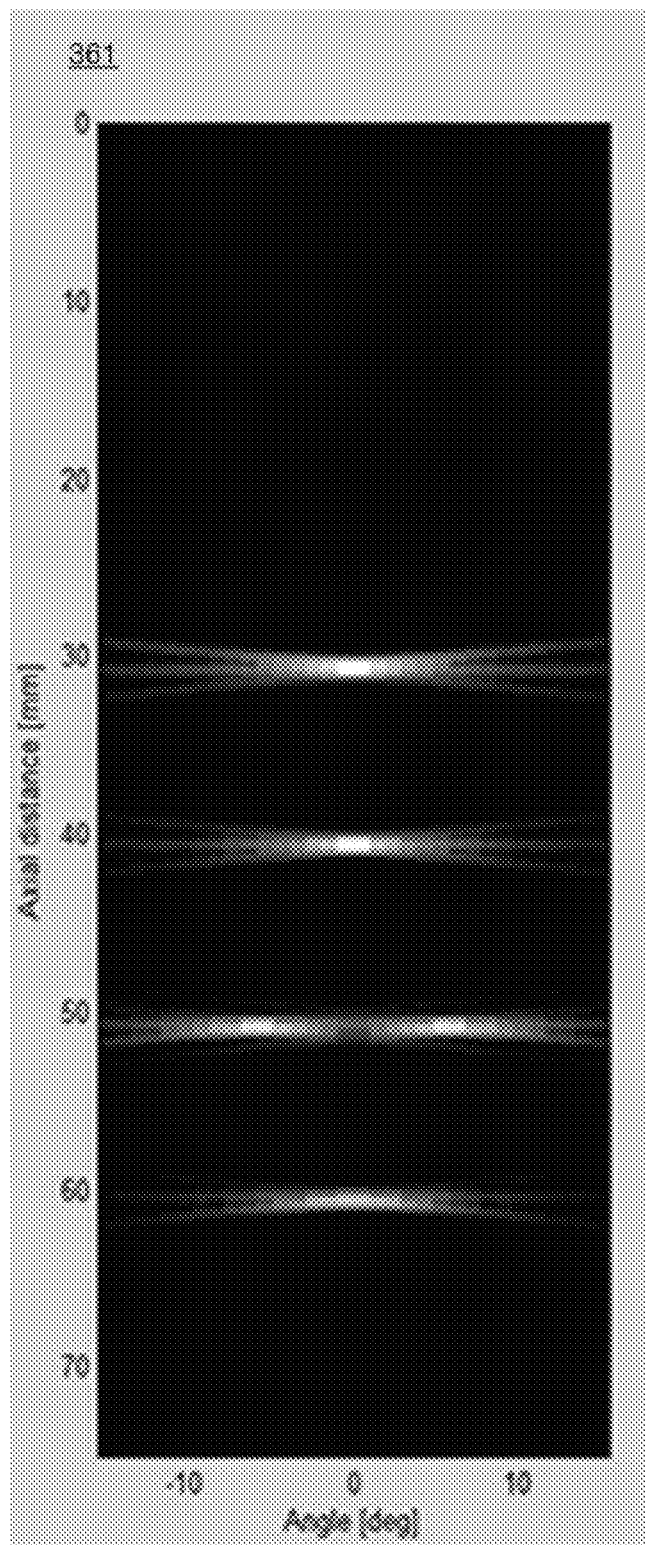
FIG. 10A is an illustration of an ultrasound image in the absence of motion through the ultrasound imaging apparatus according to an embodiment.
Figure 10B:
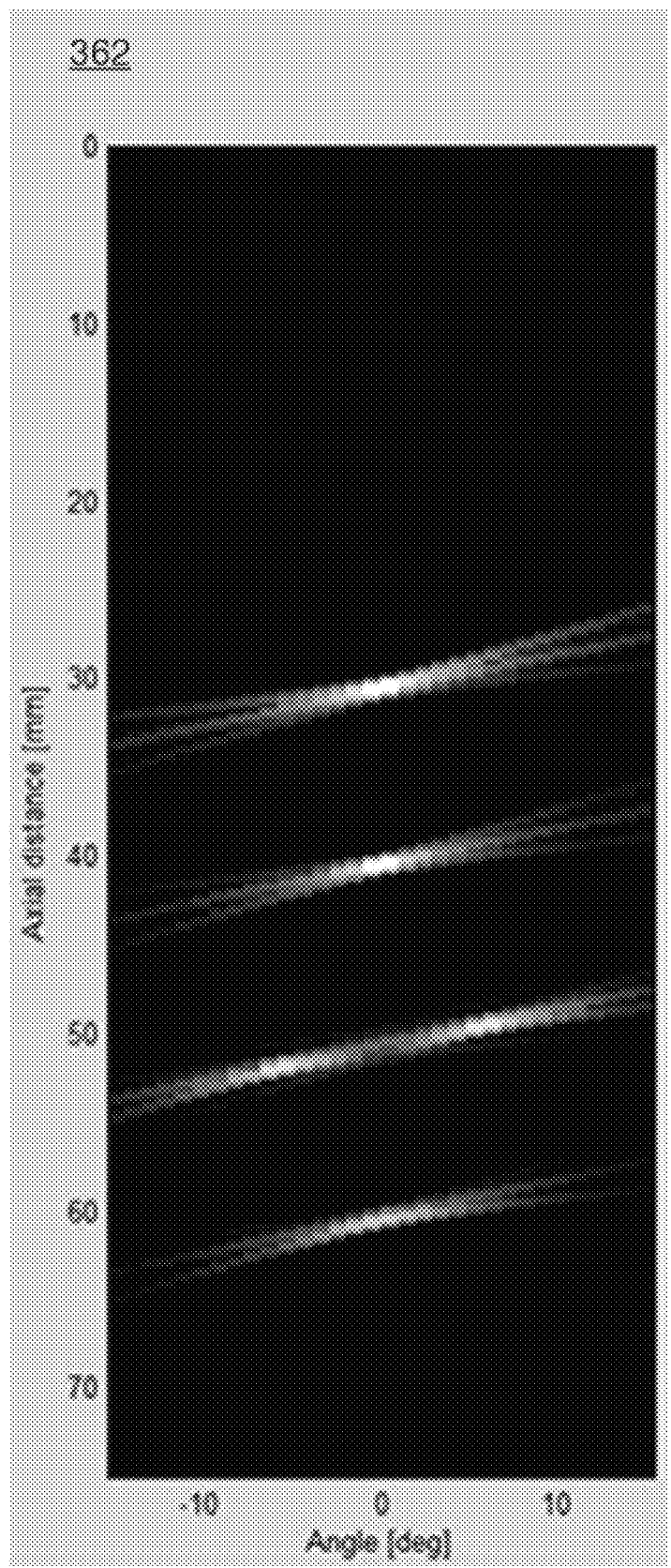
FIG. 10B is an illustration of an ultrasound image in the case where there is motion in the axial direction through the ultrasound imaging apparatus according to an embodiment.
Figure 10C:
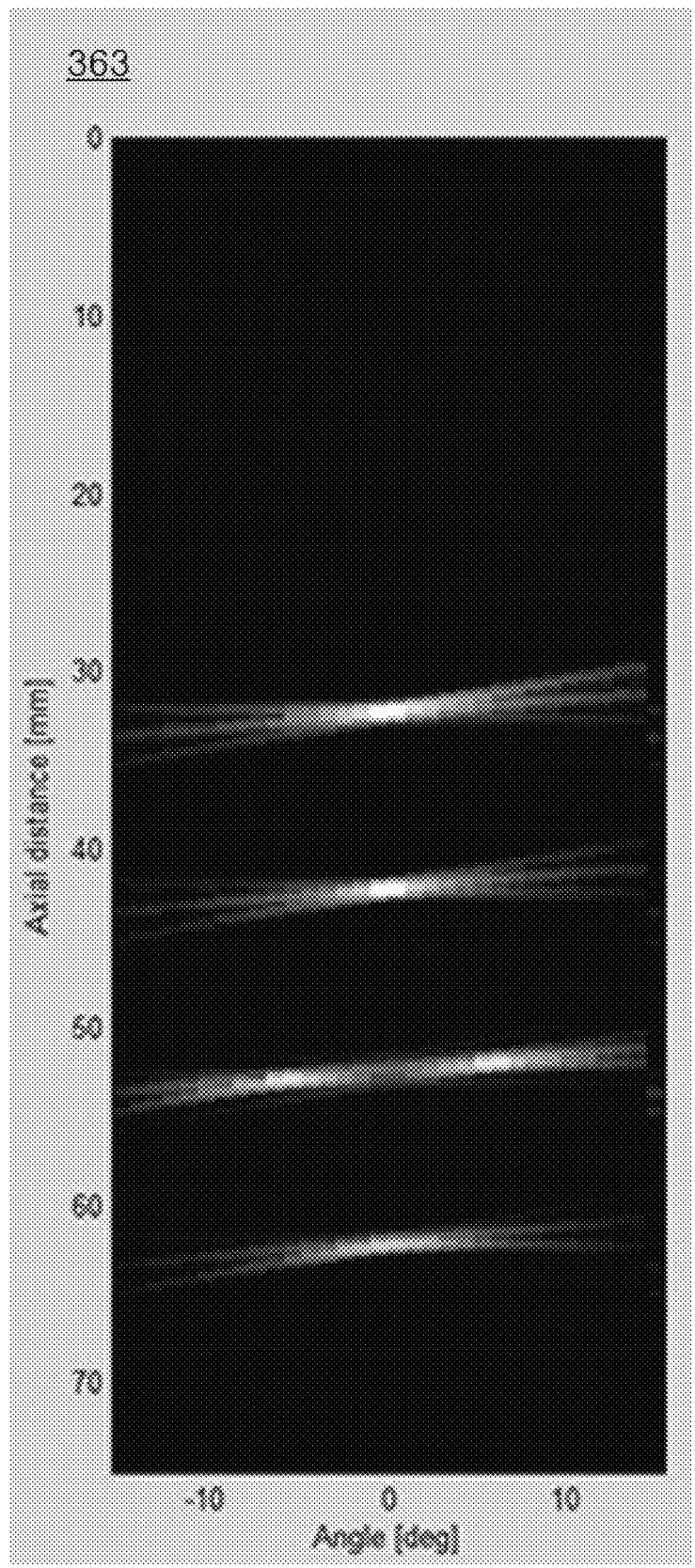
FIG. 10C is an example of an ultrasound image interpolated when there is motion in the axial direction through the ultrasound imaging apparatus according to an embodiment.

FIG. 10A 10A is an illustration of an ultrasound image in the absence of motion through the ultrasound imaging apparatus, FIG. 10B is an illustration of an ultrasound image in the absence of an ultrasound image in a case where there is an axis in an axial direction through the ultrasound imaging apparatus and FIG. 100 is an illustration of an ultrasound image in the absence of an ultrasound image interpolated when there is motion in the axial direction through the imaging device.

As shown in FIG. 10A, the ultrasonographic image of the target area without motion is measured in a state of being focused at a desired position parallel to the lateral axis.

As shown in FIG. 10b, The ultrasound image obtained by measuring an object having a motion in the axial direction can be measured in a state in which the ultrasound image is not parallel to the lateral axis but is focused at an undesired position by the user. Accordingly, the ultrasound imaging apparatus divides the target portion having the motion in the axial direction into a plurality of groups, and reduces the distortion by sampling the beamforming output signals of the respective groups based on the divided motion vectors.

An embodiment in which the ultrasound imaging apparatus measures a 3D volume to process a 3D ultrasound image will be described by reference to FIGS. 11 to 15.

Figure 11:
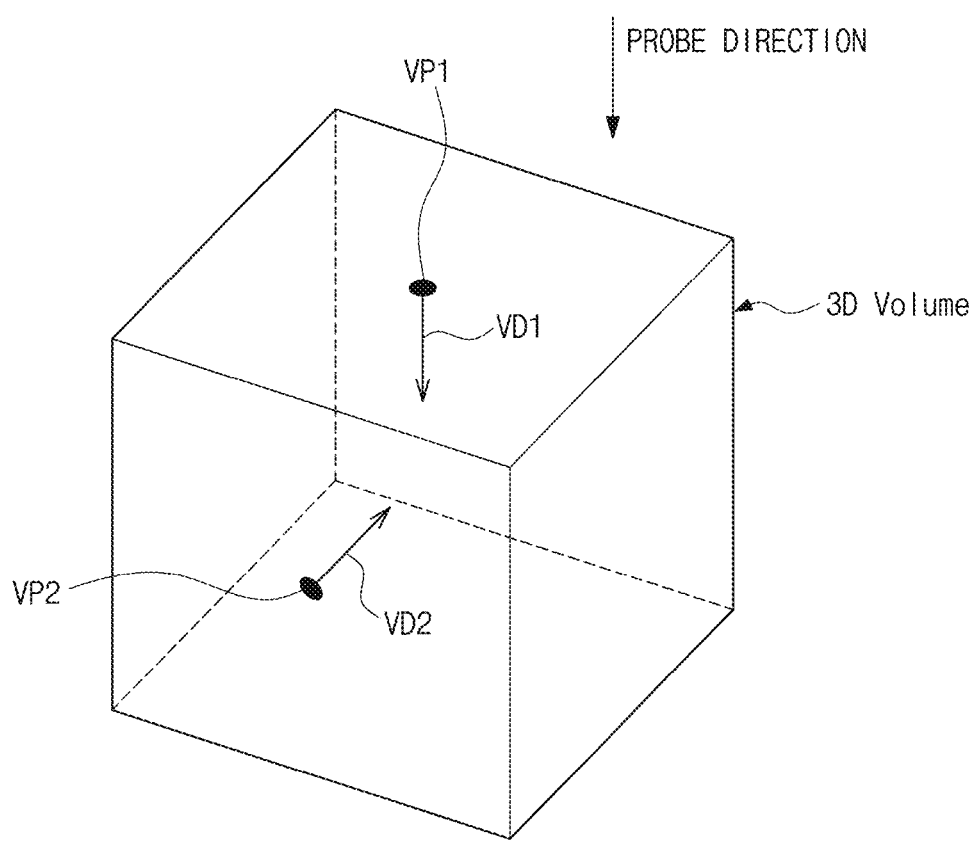
FIG. 11 is a conceptual diagram for explaining a 3D volume and observation information according to an embodiment.

FIG. 11 is a conceptual diagram for explaining a 3D volume and observation information.

Here, the 3D volume may be composed of elements called voxels.

A voxel is a compound of volume and pixel. If a pixel defines a point in a two-dimensional plane, the voxel can define a point in a 3D space.

That is, unlike pixels that can be represented by x and y coordinates, voxels can be represented by x, y, and z coordinates.

As shown in FIG. 11, the ultrasonic probe 10 can probe a 3D volume.

At this time, the 3D volume is composed of a plurality of voxels.

At this time, the reception beamformer 120 detects the voxel (VP1) corresponding to the center of the voxel closest to the axial direction, which is the probe direction of the probe, as the observation center, and detects the depth direction of the probe as the observation direction (VD1).

In addition, the observation information can be changed according to the input of the user. For example, when the user changes from the observation center VP1 to VP2 and changes the observation direction from VD1 to VD2, the observation information can be changed even if the probe direction of the probe does not change.

Figure 12:
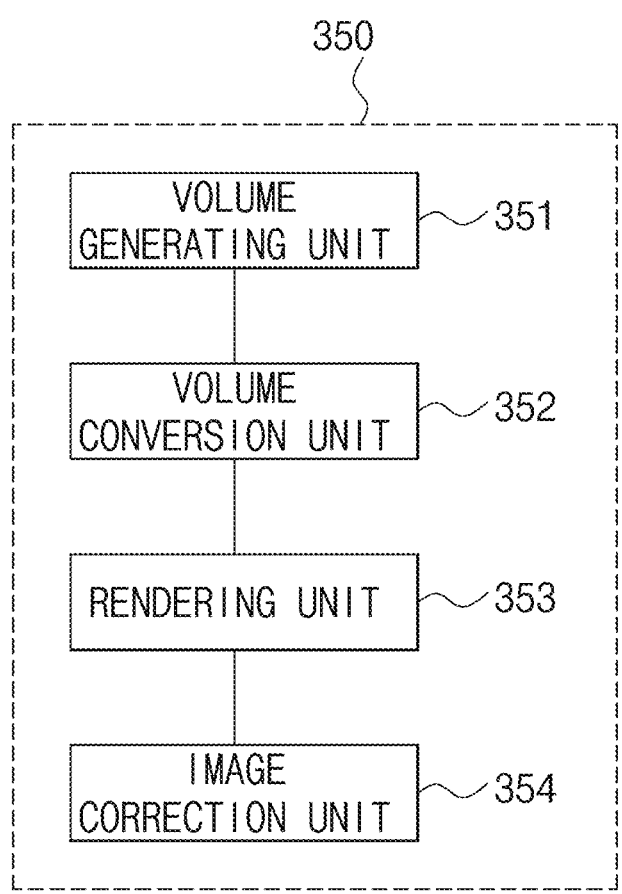
FIG. 12 is a block diagram for explaining the configurations of a 3D mode processing unit according to an embodiment.

"FIG. 12 is a block diagram for explaining the configurations of a 3D mode processing unit.

The 3D mode processing unit 350 may combine one or more output signals output from the reception beamformer 120 to generate a 3D volume, render the generated 3D volume, and output the generated 3D volume.

The 3D mode processing unit 350 may include a volume generating unit 351, a volume conversion unit 352, a rendering unit 353, and an image correction unit 354.

The volume generating unit 351 may combine one or more two-dimensional images to generate a 3D volume. As described above, the 3D volume can be generated in various ways. For convenience of explanation, the 3D volume is generated by data interpolation.

Figure 13:
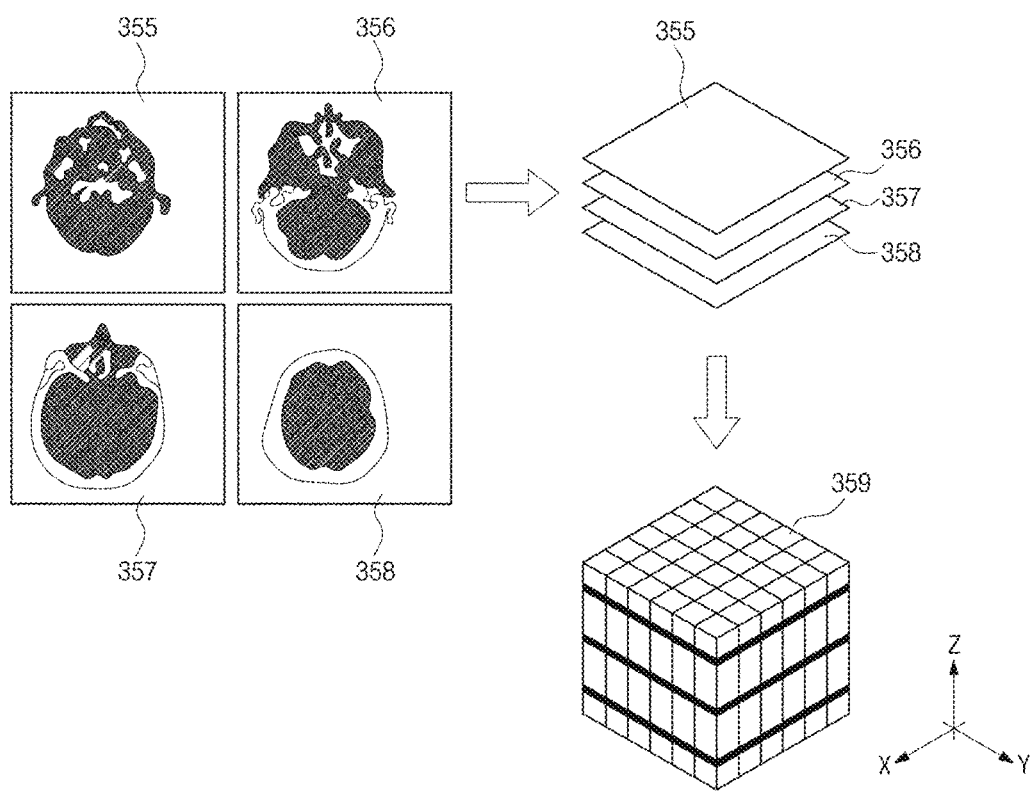
FIG. 13 is a conceptual diagram for explaining creation of a 3D volume according to an embodiment.

FIG. 13 is a conceptual diagram for explaining creation of a 3D volume.

The volume generating unit 351 may acquire a plurality of two-dimensional sectional images 355, 356, 357, and 358 based on one or more output signals received from the reception beamformer 120.

The volume generating unit 351 rearranges the obtained two-dimensional sectional images 355, 356, 357, and 358, and the volume generating unit 351 may generate a 3D volume 359 while data interpolating a value between the sectional images. At this time, the 3D volume can be generated in the form of a matrix. That is, each voxel can be represented by an XYZ-axis. On the other hand, each voxel can be expressed as a scalar value or a vector value.

More specifically, when a voxel value consists only of a binary representation of 0 or 1, a 3D volume is generated in a binary volume data format, or a voxel value is expressed in a multi-volume volume data format that can be represented by a measurable value such as density or temperature. A 3D volume can be created.

Also, the values of the optical elements of the voxel such as the opacity value and the color value can be obtained by using the voxel value.

The opacity value can be calculated by an opacity transfer function that defines the relationship between the voxel value and the opacity value.

The color value can be calculated by a color transfer function that defines the relationship between the voxel value and the color value, respectively.

Figure 14:
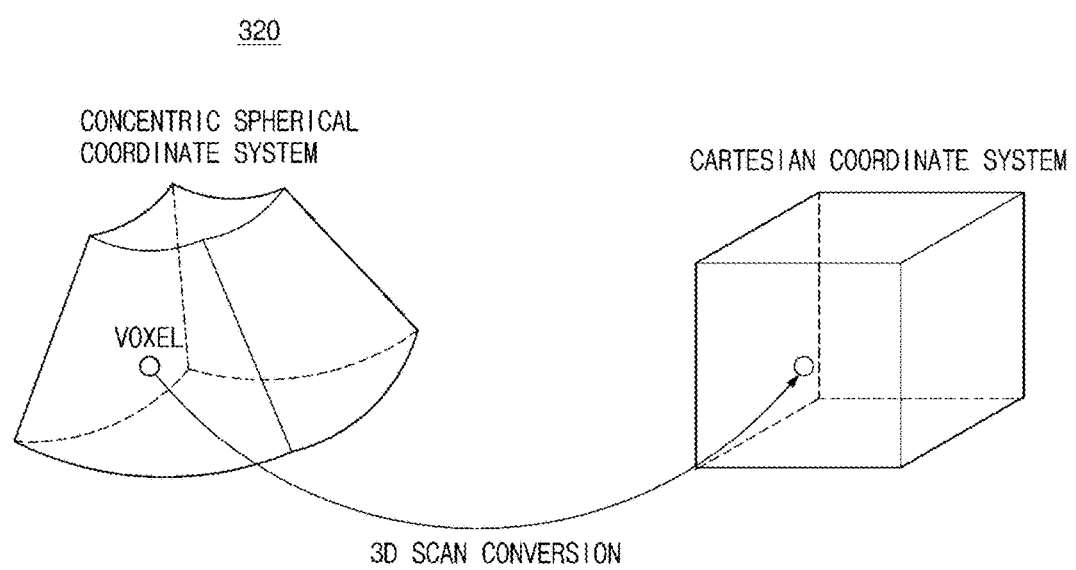
FIG. 14 is a conceptual diagram for explaining a 3D volume conversion according to an embodiment.

FIG. 14 is a conceptual diagram for explaining a 3D volume conversion.

The volume conversion unit 352 may perform scan conversion of the 3D volume.

If the ultrasonic probe 10 is in a linear form according to an embodiment, a different volume conversion may be unnecessary. However, when the ultrasonic probe 10 is in another form such as a convex shape, it is necessary to convert the volume to a rectangular coordinate system. Specifically, since the display screen uses an orthogonal coordinate system, in order to visualize the volume of the object on the display screen, the volume also has to be a rectangular coordinate system.

As shown in the left side of FIG. 14, when the volume generated from the volume generating unit 351 is in the form of a concentric spherical coordinate system, a coordinate conversion process is required in the process of visualizing the volume on the display screen.

Figure 15:
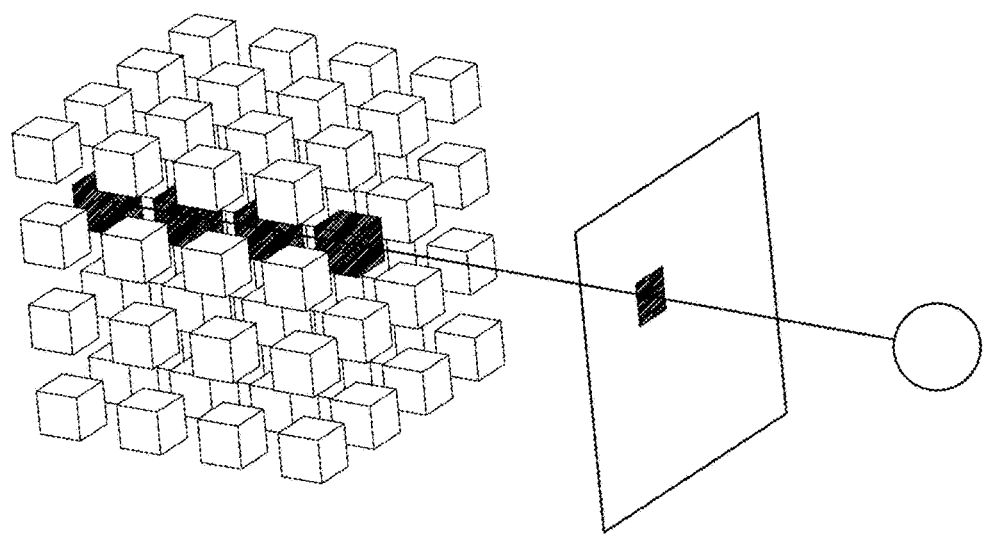
FIG. 15 is a conceptual diagram for explaining rendering performed in the ultrasound imaging apparatus according to an embodiment.

FIG. 15 is a conceptual diagram for explaining rendering performed in the ultrasound imaging apparatus.

The rendering unit 353 may perform volume rendering based on the 3D volume and generate a projection image for the object.

More specifically, the rendering unit 353 visualizes the 3D volume as a 3D image. The volume rendering method can be roughly divided into a surface rendering method and a direct rendering method.

The surface rendering method can estimate the surface information based on the scalar value and the spatial variation amount set by the user from the volume.

Then, the surface rendering method can be visualized by converting it into a geometric element such as a polygon or a surface patch. Representative surface rendering methods include the marching cubes algorithm.

Direct rendering is a way to directly visualize the volume without intervening the surface into a geometric element. The direct rendering method can be divided into an image-order algorithm and an object-order algorithm according to the method of searching volume.

The object order algorithm is a method of searching the volume according to the storage order and compositing each voxel to the corresponding pixel. A typical example of the object order algorithm is a splatting method.

The image sequence algorithm determines each pixel value in the order of the scan lines of the image. The image sequence algorithm is a method of sequentially determining pixel values corresponding to a volume along rays starting from each pixel. Ray casting and ray tracing are typical examples of image sequence algorithms.

Hereinafter, with reference to FIG. 16, a description will be made of a control method in which an ultrasound imaging apparatus divides a group of target sites, samples a beamforming output signal for each group, and then matches and synthesizes the sampled signals.

Figure 16:
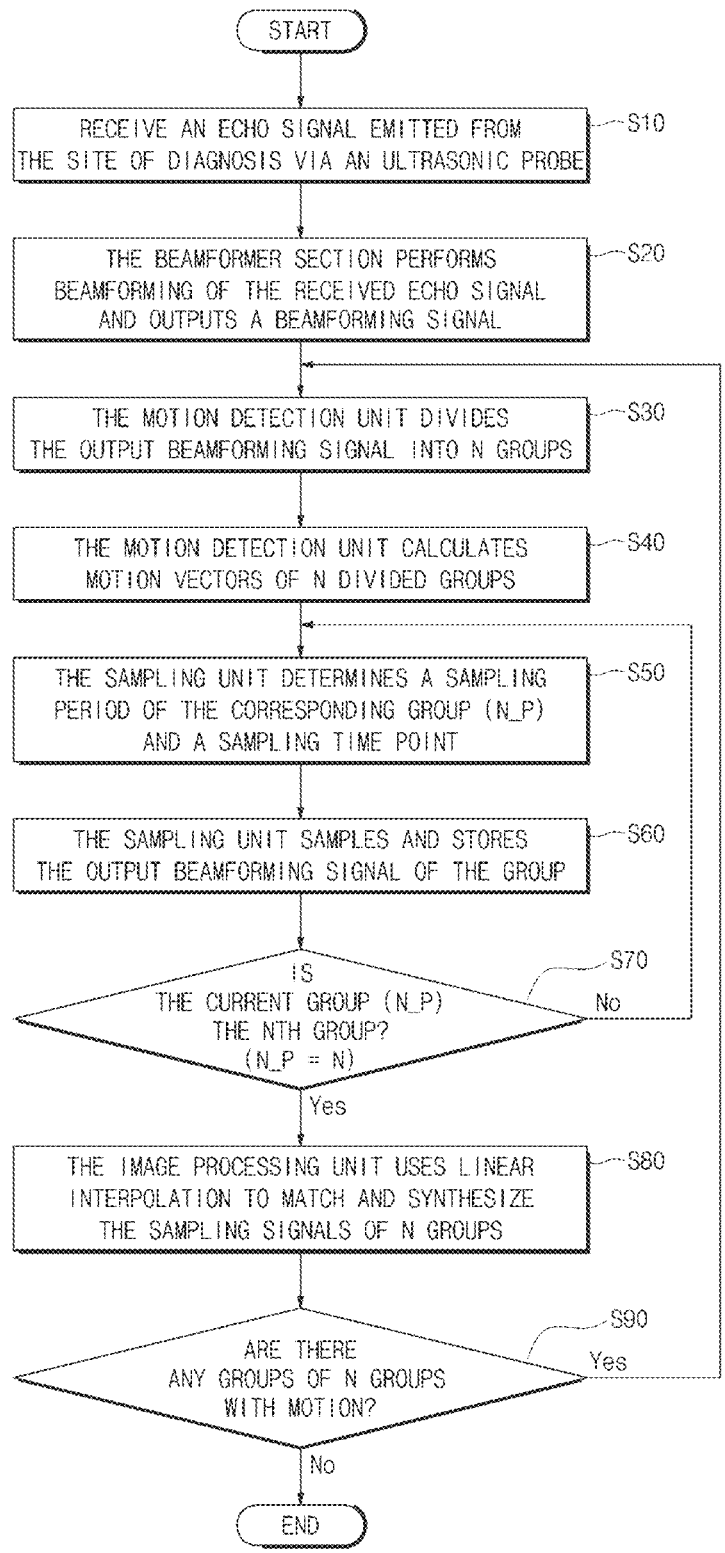
FIG. 16 is a flowchart illustrating a method of adjusting a sampling of a beamforming output signal according to a detected motion vector by detecting a motion vector of each group by dividing a target region into groups according to an exemplary embodiment, and a control method of the ultrasound imaging apparatus to be combined.

FIG. 16 is a flowchart illustrating a control method of the ultrasound imaging apparatus. The flowchart relates to dividing target portions into groups, detecting motion vectors of each group, adjusting the sampling of the beamforming output signal according to the detected motion vectors, and matching and synthesizing the sampling signals of each group. The ultrasound imaging apparatus may emit ultrasound generated at the target site through the ultrasound probe and receive the reflected ultrasound echo signal at the target site (S 10). Then, the reception beamformer of the beamforming unit converts the received echo signal into a digital signal, compensates the delay time, and focuses the echo signal to output a beamforming signal (S 20).

The motion detection unit may divide (S 30) the beamforming signals output from the input unit of the user or the number of divisions or other divisions set in the system into n groups. The motion detection unit calculates a motion vector by cross-correlating a signal obtained by interpolating a beamforming output signal or a sampling signal of a plurality of groups of n divided groups with a signal of another group or previous time (S 40).

Thereafter, the sampling unit may determine the sampling period and the sampling time of the group (n_p) according to the calculated motion vector (S50), and sample and store the beamforming output signal of the group (n_p) (S60).

If the sampling operation of the corresponding group is performed, the controller determines whether the current group (n_p) is the nth group (n_p=n) (S70). If the current group (n_p) is not the nth group it is possible to control the operations of S 50 and S 60 of the next group.

However, if the current group n_p is the n-th group, the image processing unit can perform the matching and synthesis of the sampling signals of n groups using linear interpolation (S 80).

When the sampling signals are matched and synthesized, the motion detection unit can determine whether there is a motion group among the n groups (S 90). The motion detection unit may perform the operations of S30 to S80 again if there is a group of motion-enabled groups. The motion detection unit may terminate the operation when there is no group with motion. It will be apparent to those skilled in the art that various modifications, substitutions, and alterations can be made hereto without departing from the spirit and scope of the invention as defined by the appended claims.

Therefore, the embodiments and the accompanying drawings described above are intended to illustrate and not limit the technical idea, and the scope of technical thought is not limited by these embodiments and the accompanying drawings.

The scope of which is to be interpreted by the following claims, and all technical ideas which are within the scope of the same should be interpreted as being included in the scope of the right.

The invention claimed is:

1. An ultrasound imaging apparatus comprising:
an ultrasonic probe configured to transmit ultrasonic waves towards a target region, and receive echo signals reflected by the target region; and
a controller configured to:
obtain beamformed signals corresponding to the target region, based on the echo signals;
divide the target region and the beamformed signals into a predetermined number of groups;
determine respective motion vectors for each of the predetermined number of groups;
sample the beamformed signals using different sampling periods for each of the predetermined number of groups, based on the respective motion vectors, by adjusting a first sampling period of first beamformed signals corresponding to a first group to be less than a predetermined period based on a first motion vector of the first group being greater than a predetermined value, and by adjusting a second sampling period of second beamformed signals of a second group to be greater than the predetermined period based on a second motion vector of the second group being less than the predetermined value; and
generate an ultrasound image by matching and synthesizing the sampled beamformed signals, and by using linear interpolation for a time period during which the first beamformed signals are sampled and during which the second beamformed signals are not sampled,
wherein the first sampling period is a first time difference between consecutive samples of the first beamformed signals,
wherein the second sampling period is a second time difference between consecutive samples of the second beamformed signals, and
wherein the controller, when generating the ultrasound image by matching and synthesizing the sampled beamformed signals, is configured to:

generate a first ultrasound image signal for a first time by spatial matching the first beamformed signals and the second beamformed signals simultaneously sampled at the first time, interpolate the second beamformed signals for a second time by temporal matching the second beamformed signals sampled at the first time, when the first beamformed signals are sampled at the second time and the second beamformed signals are not sampled at the second time, generate a second ultrasound image signal for the second time by spatial matching the first beamformed signals sampled at the second time and the interpolated second beamformed signals at the second time, and generate the ultrasound image by synthesizing the first ultrasound image signal and the second ultrasound image signal.

2. The ultrasound imaging apparatus according to claim 1, wherein the controller is further configured to:
compare the beamformed signals of the predetermined number of groups; and
calculate the respective motion vectors based on comparing the beamformed signals.

3. The ultrasound imaging apparatus according to claim 2, wherein the controller is further configured to:
compare the beamformed signals of the predetermined number of groups with previous beamformed signals of the predetermined number of groups; and
calculate the respective motion vectors based on comparing the beamformed signals with the previous beamformed signals.

4. The ultrasound imaging apparatus according to claim 1, wherein the controller is further configured to:
sample the beamformed signals using different sampling times for the first group and the second group based on the respective motion vectors.

5. The ultrasound imaging apparatus according to claim 2, wherein the controller is further configured to:
divide groups located at an adjacent elevation into different groups.

6. The ultrasound imaging apparatus according to claim 1, wherein the controller is further configured to:
interpolate the beamformed signals using linear interpolation; and
determine the respective motion vectors based on the interpolated beamformed signals.

7. The ultrasound imaging apparatus according to claim 1, wherein the controller is further configured to:
interpolate the second beamformed signals using linear interpolation; and
replace sampled signals of the second group with interpolated signals of the second group based on the second motion vector of the second group being less than the predetermined value.

8. A control method for an ultrasound imaging apparatus, the method comprising:
controlling a probe to transmit ultrasonic waves towards a target region;
controlling the probe to receive echo signals reflected by the target region;
obtaining beamformed signals corresponding to the target region, based on the echo signals;
dividing the target region and the beamformed signals into a predetermined number of groups;
determining respective motion vectors for each of the predetermined number of groups;

sampling the beamformed signals using different sampling periods for each of the predetermined number of groups, based on the respective motion vectors, by adjusting a first sampling period of first beamformed signals corresponding to a first group to be less than a predetermined period based on a first motion vector of the first group being greater than a predetermined value, and by adjusting a second sampling period of second beamformed signals of a second group to be greater than the predetermined period based on a second motion vector of the second group being less than the predetermined value; and generating an ultrasound image by matching and synthesizing the sampled beamformed signals, and by using linear interpolation for a time period during which the first beamformed signals are sampled and during which the second beamformed signals are not sampled, wherein the first sampling period is a first time difference between consecutive samples of the first beamformed signals, wherein the second sampling period is a second time difference between consecutive samples of the second beamformed signals, wherein the generating the ultrasound image by matching and synthesizing the sampled beamformed signals comprises:

generating a first ultrasound image signal for a first time by spatial matching the first beamformed signals and the second beamformed signals simultaneously sampled at the first time, , interpolating the second beamformed signals for a second time by temporal matching the second beamformed signals sampled at the first time, when the first beamformed signals are sampled at the second time and the second beamformed signals are not sampled at the second time, generating a second ultrasound image signal for the second time by spatial matching the first beamformed signals sampled at the second time and the interpolated second beamformed signals at the second time, and generating the ultrasound image by synthesizing the first ultrasound image signal and the second ultrasound image signal.

9. The method according to claim 8, further comprising, comparing the beamformed signals of the predetermined number of groups; and calculating the respective motion vectors based on comparing the beamformed signals.

10. The method according to claim 9,
wherein calculating the respective motion vectors comprises calculating the respective motion vectors by comparing the beamformed signals of the predetermined number of groups and previous beamforming signals of the predetermined number of groups.

11. The method according to claim 8,
wherein sampling the beamformed signals comprises sampling using different sampling times for the first group and the second group.

12. The method according to claim 9,
wherein dividing the beamforming signals into the predetermined number of groups comprises dividing the beamformed signals into different groups located at close elevations.

13. The method according to claim 8, further comprising:
interpolating the beamformed signals for each of the predetermined number of groups using a linear interpolation method; and determining the respective motion vectors based on interpolating the beamformed signals.

14. The method according to claim 8, further comprising:
interpolating the beamformed signals for the second group using a linear interpolation method; and
replacing sampled signals of the second group having the second motion vector that is less than or equal to the predetermined value with the interpolated signals of the second group having the second motion vector that is less than or equal to the predetermined value.

15. The imaging apparatus of claim 1, wherein the predetermined number of groups of the target region comprise spatial groups, and the sampling periods are based on the respective motion vectors of the spatial groups.

\* \* \* \* \*